(12) United States Patent
    Schirok et al.

(10) Patent No.: US 9,670,202 B2
(45) Date of Patent: Jun. 6, 2017

(54) SUBSTITUTED TRIAZOLOPYRIDINES

(71) Applicant: BAYER PHARMA AKTIENGESELLSCHAFT, Berlin (DE)

(72) Inventors: Hartmut Schirok, Langenfeld (DE); Volker Schulze, OT Bergf (DE); Dirk Kosemund, Berlin (DE); Hans Briem, Berlin (DE); Benjamin Bader, Berlin (DE); Ulf Bömer, Glienicke (DE); Antje Margret Wengner, Berlin (DE); Gerhard Siemeister, Berlin (DE); Philip Lienau, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/896,426

(22) PCT Filed: Jun. 3, 2014

(86) PCT No.: PCT/EP2014/061410
    § 371 (c)(1),
    (2) Date: Dec. 7, 2015

(87) PCT Pub. No.: WO2014/195274
    PCT Pub. Date: Dec. 11, 2014

(65) Prior Publication Data
    US 2016/0297811 A1   Oct. 13, 2016

(30) Foreign Application Priority Data
    Jun. 7, 2013 (EP) ..................... 13171039

(51) Int. Cl.
    C07D 471/04    (2006.01)
    A61K 31/496    (2006.01)
    A61K 31/5377   (2006.01)
    A61K 45/06     (2006.01)

(52) U.S. Cl.
    CPC .......... C07D 471/04 (2013.01); A61K 31/496 (2013.01); A61K 31/5377 (2013.01); A61K 45/06 (2013.01)

(58) Field of Classification Search
    CPC ........................... C07D 471/04; C07D 471/02
    See application file for complete search history.

Primary Examiner — Samira Jean-Louis
(74) Attorney, Agent, or Firm — Morrison & Foerster LLP

(57) ABSTRACT

The present invention relates to substituted triazolopyridine compounds of general formula (I); in which $R^1$, $R^2$, $R^3$, $R^4$, and $R^5$ are as given in the description and in the claims, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

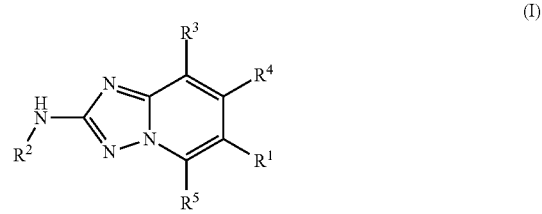

(I)

16 Claims, No Drawings

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: biotinylated peptide of the amino-acid sequence
      PWDPDDADITEILG

<400> SEQUENCE: 1

Pro Trp Asp Pro Asp Asp Ala Asp Ile Thr Glu Ile Leu Gly
1               5                   10
```

SUBSTITUTED TRIAZOLOPYRIDINES

CROSS REFERENCE TO RELATED APPLICATIONS

This application is a National Phase application under 35 U.S.C. §371 of International Application No. PCT/EP2014/061410 filed Jun. 3, 2014, which claims priority benefit to European Application No. 13171039.4 filed Jun. 7, 2013, the disclosures of each which are herein incorporated by reference in their entireties.

The present invention relates to substituted triazolopyridine compounds of general formula (I) as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, UK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of a complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumorigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81].

Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Different compounds have been disclosed in prior art which show an inhibitory effect on Mps-1 kinase:

WO 2009/024824 A1 discloses 2-Anilinopurin-8-ones as inhibitors of Mps-1 for the treatment of proliferate disorders. WO 2010/124826 A1 discloses substituted imidazoquinoxaline compounds as inhibitors of Mps-1 kinase. WO 2011/026579 A1 discloses substituted aminoquinoxalines as Mps-1 inhibitors.

Substituted triazolopyridine compounds have been disclosed for the treatment or prophylaxis of different diseases:

WO 2008/025821 A1 (Cellzome (UK) Ltd) relates to triazole derivatives as kinase inhibitors, especially inhibitors of ITK or PI3K, for the treatment or prophylaxis of immunological, inflammatory or allergic disorders. Said triazole derivatives are exemplified as possessing an amide, urea or aliphatic amine substituent in position 2.

WO 2009/047514 A1 (Cancer Research Technology Limited) relates to [1,2,4]-triazolo-[1,5-a]-pyridine and [1,2,4]-triazolo-[1,5-c]-pyrimidine compounds which inhibit AXL receptor tyrosine kinase function, and to the treatment of diseases and conditions that are mediated by AXL receptor tyrosine kinase, that are ameliorated by the inhibition of AXL receptor tyrosine kinase function etc., including proliferative conditions such as cancer, etc. Said compounds are exemplified as possessing a substituent in the 5-position and a substituent in the 2-position.

WO 2009/010530 A1 discloses bicyclic heterorayl compounds and their use as phosphatidylinositol (PI) 3-kinase. Among other compounds also substituted triazolopyridines are mentioned.

WO 2009/027283 A1 discloses triazolopyridine compounds and their use as ASK (apoptosis signal-regulating kinase) inhibitors for the treatment of autoimmune diseases and neurodegenerative diseases.

WO 2010/092041 A1 (Fovea Pharmaceuticals SA) relates to [1,2,4]-triazolo-[1,5-a]-pyridines, which are said to be useful as selective kinase inhibitors, to methods for producing such compounds and methods for treating or ameliorating kinase-mediated disorder. Said triazole derivatives are exemplified as possessing a 2-chloro-5-hydroxyphenyl substituent in the 6-position of the [1,2,4]-triazolo-[1,5-a]-pyridine.

WO 2011/064328 A1, WO 2011/063907 A1, WO 2011/063908 A1, WO 2012/143329 A1 and WO 2013/087579 A1 relate to [1,2,4]-triazolo-[1,5-a]-pyridines and their use for inhibition of Mps-1 kinase.

However, the state of the art described above does not specifically disclose the substituted triazolopyridine compounds of general formula (I) of the present invention, or a tautomer, an N-oxide, a hydrate, a solvate, or a salt thereof, or a mixture of same, as described and defined herein, and as hereinafter referred to as "compounds of the present invention", or their pharmacological activity.

SUMMARY OF THE INVENTION

The present invention covers compounds of general formula (I):

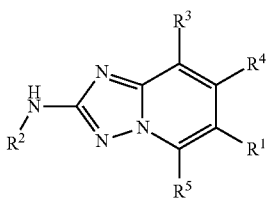

in which:

$R^1$ represents a

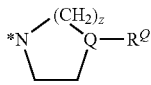

group;
wherein * indicates the point of attachment of said group with the rest of the molecule;

Q represents CH or N; with the proviso that Q represents CH if $R^Q$ represents —N(H)C(=O)$R^6$, —N(H)C(=O)N(H)$R^6$ or —N(H)C(=O)N$R^6R^7$;

$R^Q$ represents a group selected from:
—N(H)C(=O)$R^6$, —N(H)C(=O)N(H)$R^6$, —N(H)C(=O)N$R^6R^7$, —C(=O)N(H)$R^6$, —C(=O)N$R^6R^7$;

$R^2$ represents a phenyl- or pyridyl-group which is substituted one or more times, identically or differently, with a substituent selected from $R^{5a}$ and $R^{5b}$;

$R^3$ represents a hydrogen atom;
$R^4$ represents a hydrogen atom;
$R^5$ represents a hydrogen atom;

$R^{5a}$ represents a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —N$R^7R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^{5b}$ represents a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —N$R^7R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^6$ represents a group selected from:
—$(CH_2)_q$-aryl, —$(CH_2)_q$-heteroaryl, —$(CH_2)_q$—($C_3$-$C_6$-cycloalkyl), —$(CH_2)_q$-(3- to 10-membered heterocycloalkyl);
wherein said group is optionally substituted, one or more times, identically or differently, with a substituent selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —NH$_2$, —N(H)$R^8$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^7$ represents a $C_1$-$C_3$-alkyl-group or a $C_3$-$C_6$-cycloalkyl-group;

$R^8$ represents a $C_1$-$C_6$-alkyl- or —$(CH_2)_q$—$C_3$-$C_6$-cycloalkyl-group;
wherein said $C_1$-$C_6$-alkyl- or $C_3$-$C_6$-cycloalkyl-group is optionally substituted, one or more times, identically or differently, with a substituent selected from:
halo-, hydroxy-, —NH$R^7$, —N$R^7R^7$, —N($C_1$-$C_3$-alkyl)-C(=O)$R^7$, —N($C_1$-$C_3$-alkyl)-C(=O)O$R^7$, $C_1$-$C_3$-alkyl-, $R^7$—S(=O)$_2$—, $C_1$-$C_3$-alkoxy-, halo-$C_1$-$C_3$-alkoxy-;

or $R^7$ and $R^8$ together with the molecular fragment they are attached to represent a 4- to 6-membered heterocycloalkyl-group, which is optionally substituted, one or more times, identically or differently, with a halogen atom, a $C_1$-$C_3$-alkyl-, halo-$C_1$-$C_3$-alkyl- or $C_1$-$C_3$-alkoxy-group;

n, m, p,
represent, independently from each other, an integer of 0, 1, 2 or 3;

q represents an integer of 0, 1, 2 or 3;
and
z represents an integer of 1 or 2;
or a stereoisomer, a tautomer, an N-oxide, a hydrate, a solvate, or a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more of the hydrogen atoms is replaced, in identically or differently, by a halogen atom. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "hydroxy-$C_1$-$C_6$-alkyl-" is to be understood as preferably meaning a linear or branched, saturated, monovalent hydrocarbon group in which the term "$C_1$-$C_6$-alkyl-" is defined supra, and in which one or more of the hydrogen atoms is replaced by a hydroxy group with the proviso that not more than one hydrogen atom attached to a single carbon atom is being replaced. Said hydroxy-$C_1$-$C_6$-alkyl-group is, for example, —$CH_2OH$, —$CH_2CH_2$—OH, —$C(OH)H$—$CH_3$, or —$C(OH)H$—$CH_2OH$.

The term "$C_1$-$C_6$-alkoxy" is to be understood as preferably meaning a linear or branched, saturated, monovalent group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Particularly, said ring contains 3, 4, 5 or 6 carbon atoms ("$C_3$-$C_6$-cycloalkyl").

The term "$C_4$-$C_8$-cycloalkenyl" is to be understood as preferably meaning a monovalent, monocyclic hydrocarbon ring which contains 4, 5, 6, 7 or 8 carbon atoms and one or two double bonds, in conjugation or not, as the size of said cycloalkenyl ring allows. Particularly, said ring contains 4, 5 or 6 carbon atoms ("$C_4$-$C_6$-cycloalkenyl"). Said $C_4$-$C_8$-cycloalkenyl group is for example a cyclobutenyl, cyclopentenyl, or cyclohexenyl group.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, 5 or 6 carbon atoms, and one or more of the above-mentioned heteroatom-containing groups (a "3- to 7-membered heterocycloalkyl"), more particularly said heterocycloalkyl can contain 4, 5 or 6 carbon atoms, and one or more of the above-mentioned heteroatom-containing groups (a "4- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a biphenyl group (a "$C_{12}$-aryl" group), or a ring having 13 carbon atoms, (a "$C_{13}$-aryl" group), e.g. a fluorenyl group, or a ring having 14 carbon atoms, (a "$C_{14}$-aryl" group), e.g. an anthracenyl group. Preferably, the aryl group is a phenyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridyl includes pyridin-2-yl, pyridin-3-yl, and pyridin-4-yl; or the term thienyl includes thien-2-yl and thien-3-yl. Preferably, the heteroaryl group is a pyridyl group.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "$PG^1$" refers to a protecting group for hydroxy groups e.g. a TMS group or TBDPS group as described for example in T. W. Greene and P. G. M. Wuts in *Protective Groups in Organic Synthesis*, 3' edition, Wiley 1999 (TMS=trimethylsilyl, TBDPS=tert-butyldiphenylsilyl).

As used herein, the term "$PG^2$" refers to a protecting group for amino groups e.g. a Boc group as described for example in T. W. Greene and P. G. M. Wuts in *Protective Groups in Organic Synthesis*, 3" edition, Wiley 1999 (Boc=tert-butyloxycarbonyl).

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

The compounds of this invention contain one or more asymmetric centre, depending upon the location and nature of the various substituents desired. Asymmetric carbon atoms may be present in the (R) or (S) configuration. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

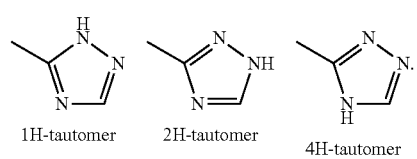

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucannine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods.

Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

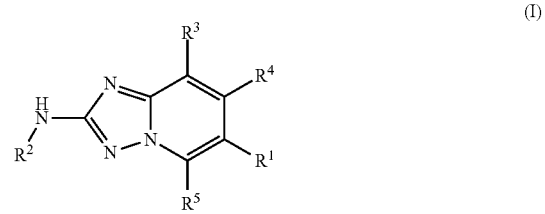

in which:
$R^1$ represents a

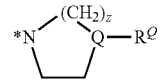

group;
  wherein * indicates the point of attachment of said group with the rest of the molecule;
Q represents CH or N; with the proviso that Q represents CH if $R^Q$ represents —N(H)C(=O)$R^6$, —N(H)C(=O)N(H)$R^6$ or —N(H)C(=O)N$R^6R^7$;
$R^Q$ represents a group selected from:
  —N(H)C(=O)$R^6$, —N(H)C(=O)N(H)$R^6$, —N(H)C(=O)N$R^6R^7$, —C(=O)N(H)$R^6$, —C(=O)N$R^6R^7$;
$R^2$ represents a phenyl- or pyridyl-group which is substituted one or more times, identically or differently, with a substituent selected from $R^{5a}$ and $R^{5b}$;
$R^3$ represents a hydrogen atom;
$R^4$ represents a hydrogen atom;
$R^5$ represents a hydrogen atom;
$R^{5a}$ represents a group selected from:
  halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —N$R^7R^7$, —C(=O)N(H)R⁸, —C(=O)NR⁸R⁷, R⁸—S—, R⁸—S(=O)—, R⁸—S(=O)₂—, —N(H)S(=O)R⁸, —N(R⁷)S(=O)R⁸, —S(=O)N(H)R⁸, —S(=O)NR⁸R⁷, —N(H)S(=O)₂R⁸, —N(R⁷)S(=O)₂R⁸, —S(=O)₂N(H)R⁸, —S(=O)₂NR⁸R⁷, —S(=O)(=NR⁸)R⁷, —S(=O)(=NR⁷)R⁸, —N=S(=O)(R⁸)R⁷;

R$^{5b}$ represents a group selected from:

halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R⁸—($C_1$-$C_6$-alkyl)-, R⁸—(CH₂)$_n$(CHOH)(CH₂)$_m$—, R⁸—($C_1$-$C_6$-alkoxy)-, R⁸—(CH₂)$_n$(CHOH)(CH₂)$_p$—O—, R⁸—($C_1$-$C_6$-alkoxy-$C_1$-$C_6$-alkyl)-, R⁸—($C_1$-$C_6$-alkoxy-$C_1$-$C_6$-alkyl)-O—, —O—(CH₂)$_n$—C(=O)NR⁸R⁷, R⁸—O—, —C(=O)R⁸, —C(=O)O—R⁸, —OC(=O)—R⁸, —N(H)C(=O)R⁸, —N(R⁷)C(=O)R⁸, —N(H)C(=O)NR⁸R⁷, —N(R⁷)C(=O)NR⁸R⁷, —NR⁸R⁷, —NR⁷R⁷, —C(=O)N(H)R⁸, —C(=O)NR⁸R⁷, R⁸—S—, R⁸—S(=O)—, R⁸—S(=O)₂—, —N(H)S(=O)R⁸, —N(R⁷)S(=O)R⁸, —S(=O)N(H)R⁸, —S(=O)NR⁸R⁷, —N(H)S(=O)₂R⁸, —N(R⁷)S(=O)₂R⁸, —S(=O)₂N(H)R⁸, —S(=O)₂NR⁸R⁷, —S(=O)(=NR⁸)R⁷, —S(=O)(=NR⁷)R⁸, —N=S(=O)(R⁸)R⁷;

R⁶ represents a group selected from:

—(CH₂)$_q$-aryl, —(CH₂)$_q$-heteroaryl, —(CH₂)$_q$—($C_3$-$C_6$-cycloalkyl), —(CH₂)$_q$-(3- to 10-membered heterocycloalkyl);

wherein said group is optionally substituted, one or more times, identically or differently, with a substituent selected from: halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R⁸—($C_1$-$C_6$-alkyl)-, R⁸—(CH₂)$_n$(CHOH)(CH₂)$_m$—, R⁸—($C_1$-$C_6$-alkoxy)-, R⁸—(CH₂)$_n$(CHOH)(CH₂)$_p$—O—, R⁸—($C_1$-$C_6$-alkoxy-$C_1$-$C_6$-alkyl)-, R⁸—($C_1$-$C_6$-alkoxy-$C_1$-$C_6$-alkyl)-O—, aryl-, R⁸—O—, —C(=O)R⁸, —C(=O)O—R⁸, —OC(=O)—R⁸, —N(H)C(=O)R⁸, —N(R⁷)C(=O)R⁸, —N(H)C(=O)NR⁸R⁷, —N(R⁷)C(=O)NR⁸R⁷, —NH₂, —N(H)R⁸, —NR⁸R⁷, —C(=O)N(H)R⁸, —C(=O)NR⁸R⁷, R⁸—S—, R⁸—S(=O)—, R⁸—S(=O)₂—, —N(H)S(=O)R⁸, —N(R⁷)S(=O)R⁸, —S(=O)N(H)R⁸, —S(=O)NR⁸R⁷, —N(H)S(=O)₂R⁸, —N(R⁷)S(=O)₂R⁸, —S(=O)₂N(H)R⁸, —S(=O)₂NR⁸R⁷, —S(=O)(=NR⁸)R⁷, —S(=O)(=NR⁷)R⁸, —N=S(=O)(R⁸)R⁷;

R⁷ represents a $C_1$-$C_3$-alkyl-group or a $C_3$-$C_6$-cycloalkyl-group;

R⁸ represents a $C_1$-$C_6$-alkyl- or —(CH₂)$_q$—$C_3$-$C_6$-cycloalkyl-group;

wherein said $C_1$-$C_6$-alkyl- or $C_3$-$C_6$-cycloalkyl-group is optionally substituted, one or more times, identically or differently, with a substituent selected from:

halo-, hydroxy-, —NHR⁷, —NR⁷R⁷, —N($C_1$-$C_3$-alkyl)-C(=O)R⁷, —N($C_1$-$C_3$-alkyl)-C(=O)OR⁷, $C_1$-$C_3$-alkyl-, R⁷—S(=O)₂—, $C_1$-$C_3$-alkoxy-, halo-$C_1$-$C_3$-alkoxy-;

or

R⁷ and R⁸ together with the molecular fragment they are attached to represent a 4- to 6-membered heterocycloalkyl-group, which is optionally substituted, one or more times, identically or differently, with a halogen atom, a $C_1$-$C_3$-alkyl-, halo-$C_1$-$C_3$-alkyl- or $C_1$-$C_3$-alkoxy-group;

n, m, p, represent, independently from each other, an integer of 0, 1, 2 or 3;

q represents an integer of 0, 1, 2 or 3;

and z represents an integer of 1 or 2;

or a stereoisomer, a tautomer, an N-oxide, a hydrate, a solvate, or a salt thereof, or a mixture of same.

In a preferred embodiment, the invention relates to compounds of formula (I), wherein R¹ represents a group selected from:

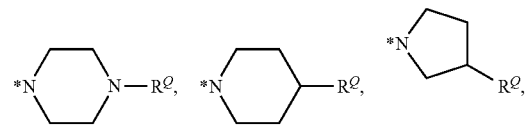

wherein * indicates the point of attachment of said group with the rest of the molecule.

In another preferred embodiment, the invention relates to compounds of formula (I), wherein R¹ represents a group selected from:

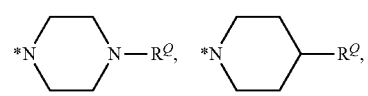

wherein * indicates the point of attachment of said group with the rest of the molecule.

In another preferred embodiment, the invention relates to compounds of formula (I), wherein R¹ represents

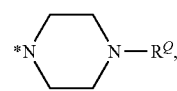

wherein * indicates the point of attachment of said group with the rest of the molecule.

In another preferred embodiment, the invention relates to compounds of formula (I), wherein R¹ represents

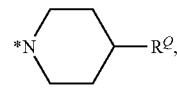

wherein * indicates the point of attachment of said group with the rest of the molecule.

In another preferred embodiment, the invention relates to compounds of formula (I), wherein R¹ represents

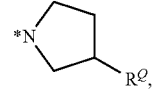

wherein * indicates the point of attachment of said group with the rest of the molecule.

In another preferred embodiment, the invention relates to compounds of formula (I), wherein Q represents N.

In another preferred embodiment, the invention relates to compounds of formula (I), wherein Q represents CH.

In another preferred embodiment, the invention relates to compounds of formula (I), wherein $R^Q$ represents a group selected from: —N(H)C(=O)R$^6$, —N(H)C(=O)N(H)R$^6$, —C(=O)N(H)R$^6$.

In another preferred embodiment, the invention relates to compounds of formula (I), wherein $R^Q$ represents —N(H)C(=O)R$^6$.

In another preferred embodiment, the invention relates to compounds of formula (I), wherein $R^Q$ represents —N(H)C(=O)N(H)R$^6$.

In another preferred embodiment, the invention relates to compounds of formula (I), wherein $R^Q$ represents —C(=O)N(H)R$^6$.

In another preferred embodiment, the invention relates to compounds of formula (I), wherein $R^Q$ represents

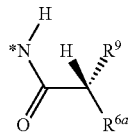

wherein * indicates the point of attachment of said group with the rest of the molecule; wherein $R^{6a}$ represents a phenyl-group which is optionally substituted, one or more times, identically or differently, with fluoro; wherein $R^9$ represents a group selected from: $C_1$-$C_3$-alkyl-, hydroxy-$C_1$-$C_3$-alkyl-, —N(H)R$^8$; —N(R$^7$)R$^8$, N(H)(R$^8$)—$C_1$-$C_3$-alkyl-, N(R$^7$)(R$^8$)—$C_1$-$C_3$-alkyl-.

In another preferred embodiment, the invention relates to compounds of formula (I), supra, wherein $R^Q$ represents a group selected from:

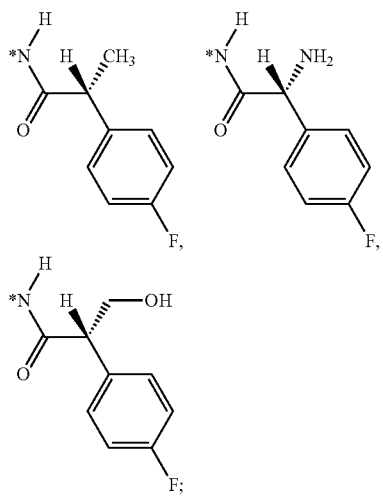

wherein * indicates the point of attachment of said groups with the rest of the molecule.

In another preferred embodiment, the invention relates to compounds of formula (I), wherein $R^2$ is selected from:

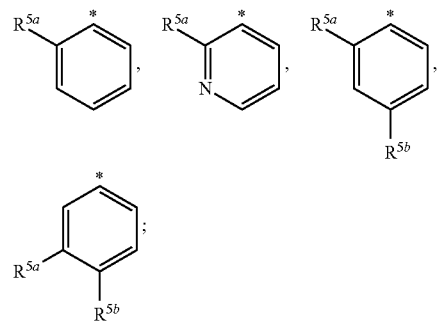

wherein * indicates the point of attachment of said groups with the rest of the molecule.

In another preferred embodiment, the invention relates to compounds of formula (I), wherein $R^2$ represents

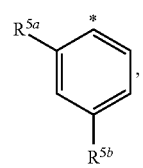

wherein * indicates the point of attachment of said groups with the rest of the molecule.

In another preferred embodiment, the invention relates to compounds of formula (I), wherein $R^{5a}$ represents a group selected from: halo-, cyano-, $C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R$^8$—($C_1$-$C_6$-alkoxy)-, R$^8$—O—, R$^8$—S—, R$^8$—S(=O)$_2$—, ($C_3$-$C_6$-cycloalkyl)-(CH$_2$)$_n$—O—.

In another preferred embodiment, the invention relates to compounds of formula (I), wherein $R^{5a}$ represents a group selected from: halo-, cyano-, $C_1$-$C_6$-alkyl-, $C_1$-$C_6$-alkoxy-, halo-$C_1$-$C_6$-alkoxy-, $C_1$-$C_6$-alkoxy-$C_1$-$C_6$-alkyl-, ($C_3$-$C_6$-cycloalkyl)-(CH$_2$)$_n$—O—.

In another preferred embodiment, the invention relates to compounds of formula (I), wherein $R^{5a}$ represents a group selected from: F—, methyl-, methoxy-, ethoxy-, n-propoxy-, iso-propoxy-, 2-methyl propoxy, cyclopropyl-O—, cyclopropyl-CH$_2$—O—, CH$_3$—O—CH$_2$CH$_2$—O—, CHF$_2$—O—, CF$_3$—O—, CF$_3$CH$_2$—O—.

In another preferred embodiment, the invention relates to compounds of formula (I), wherein $R^{5a}$ represents a group selected from: cyano-, $C_1$-$C_3$-alkoxy-, halo-$C_1$-$C_3$-alkoxy-, $C_1$-$C_3$-alkoxy-$C_1$-$C_3$-alkyl-, ($C_3$-$C_4$-cycloalkyl)-CH$_2$—O—.

In another preferred embodiment, the invention relates to compounds of formula (I), wherein $R^{5a}$ represents a group selected from: —CN, methoxy-, ethoxy-, n-propoxy-, (H$_3$C)$_2$C(H)—CH$_2$—O—, cyclopropyl-CH$_2$—O—, CH$_3$—O—CH$_2$CH$_2$—O—, CF$_3$CH$_2$—O—.

In another preferred embodiment, the invention relates to compounds of formula (I), wherein $R^{5a}$ represents a $C_1$-$C_6$-alkoxy-group.

In another preferred embodiment, the invention relates to compounds of formula (I), wherein $R^{5a}$ represents a $C_1$-$C_3$-alkoxy-group.

In another preferred embodiment, the invention relates to compounds of formula (I), wherein $R^{5a}$ represents a halo-$C_1$-$C_6$-alkoxy-group.

In another preferred embodiment, the invention relates to compounds of formula (I), wherein $R^{5a}$ represents a halo-$C_1$-$C_3$-alkoxy-group.

In another preferred embodiment, the invention relates to compounds of formula (I), wherein $R^{5a}$ represents a ($C_3$-$C_6$-cycloalkyl)-$(CH_2)_n$—O— group.

In another preferred embodiment, the invention relates to compounds of formula (I), wherein $R^{5a}$ represents a cyano-group.

In another preferred embodiment, the invention relates to compounds of formula (I), supra, wherein $R^{5a}$ represents a group selected from: $C_1$-$C_3$-alkoxy-, halo-$C_1$-$C_3$-alkoxy-, $C_1$-$C_3$-alkyl-.

In another preferred embodiment, the invention relates to compounds of formula (I), supra, wherein $R^{5a}$ represents a group selected from: $C_1$-$C_2$-alkoxy-, halo-$C_1$-$C_2$-alkoxy-, $C_1$-$C_2$-alkyl-.

In another preferred embodiment, the invention relates to compounds of formula (I), supra, wherein $R^{5a}$ represents a group selected from: $C_1$-$C_3$-alkoxy-, halo-$C_1$-$C_3$-alkoxy-.

In another preferred embodiment, the invention relates to compounds of formula (I), supra, wherein $R^{5a}$ represents a group selected from: $C_1$-$C_2$-alkoxy-, halo-$C_1$-$C_2$-alkoxy-.

In another preferred embodiment, the invention relates to compounds of formula (I), supra, wherein $R^{5a}$ represents a methoxy- or ethoxy-group which is optionally substituted, one or more times, identically or differently, with a halogen atom. The preferred halogen atom is F.

In another preferred embodiment, the invention relates to compounds of formula (I), supra, wherein $R^{5a}$ represents a group selected from: methoxy-, ethoxy-, $F_3C$—$CH_2$—O—.

In another preferred embodiment, the invention relates to compounds of formula (I), supra, wherein $R^{5a}$ represents a group selected from: methoxy-, $F_3C$—$CH_2$—O—.

In another preferred embodiment, the invention relates to compounds of formula (I), supra, wherein $R^{5a}$ represents methoxy-.

In another preferred embodiment, the invention relates to compounds of formula (I), supra, wherein $R^{5a}$ represents ethoxy-.

In another preferred embodiment, the invention relates to compounds of formula (I), supra, wherein $R^{5a}$ represents $F_3C$—$CH_2$—O—.

In another preferred embodiment, the invention relates to compounds of formula (I), wherein $R^{5b}$ represents a group selected from: halo-, cyano-, nitro-, $C_1$-$C_6$-alkyl-, halo-$C_1$-$C_6$-alkyl-, hydroxy-$C_1$-$C_6$-alkyl-, $C_1$-$C_6$-alkoxy-, halo-$C_1$-$C_6$-alkoxy-, $R^8$—O—, —C(=O)$R^8$, —C(=O)O—$R^8$, —N(H)C(=O)$R^8$, —N($R^7$)C(=O)$R^8$, —N(H)S(=O)$_2R_8$, —N$R^8R^7$, —N$R^7R^7$, —C(=O)N(H)$R^8$, —C(=O)N$R^8R^7$, $R^8$—S(=O)—, $R^8$—S(=O)$_2$—, —S(=O)(=N$R^7$)$R^8$.

In another preferred embodiment, the invention relates to compounds of formula (I), wherein $R^{5b}$ represents a group selected from: halo-, cyano-, —N$R^7R^7$, $C_1$-$C_6$-alkoxy-, —N(H)C(=O)$R^8$, —N($R^7$)C(=O)$R^8$, —C(=O)N(H)$R^8$, —C(=O)N$R^8R^7$, $R^8$—S(=O)—, $R^8$—S(=O)$_2$—, —S(=O)(=N$R^7$)$R^8$, hydroxy-$C_1$-$C_6$-alkyl-, —N(H)S(=O)$_2R^8$.

In another preferred embodiment, the invention relates to compounds of formula (I), wherein $R^{5b}$ represents a group selected from: —C(=O)N(H)$R^8$, —C(=O)N$R^8R^7$, $R^8$—S(=O)—, $R^8$—S(=O)$_2$—, —S(=O)(=N$R^7$)$R^8$.

In another preferred embodiment, the invention relates to compounds of formula (I), wherein $R^{5b}$ represents a —C(=O)N(H)$R^8$ group.

In another preferred embodiment, the invention relates to compounds of formula (I), wherein $R^{5b}$ represents a —N$R^8R^7$ group.

In another preferred embodiment, the invention relates to compounds of formula (I), wherein $R^{5b}$ represents a —C(=O)N$R^8R^7$ group.

In another preferred embodiment, the invention relates to compounds of formula (I), wherein $R^{5b}$ represents a $R^8$—S(=O)— group.

In another preferred embodiment, the invention relates to compounds of formula (I), wherein $R^{5b}$ represents a $R^8$—S(=O)$_2$— group.

In another preferred embodiment, the invention relates to compounds of formula (I), wherein $R^{5b}$ represents a —S(=O)(=N$R^7$)$R^8$ group.

In another preferred embodiment, the invention relates to compounds of formula (I), wherein $R^{5b}$ represents a —C(=O)N(H)$R^7$ group.

In another preferred embodiment, the invention relates to compounds of formula (I), wherein $R^{5b}$ represents a $R^7$—S(=O)$_2$— group.

In another preferred embodiment, the invention relates to compounds of formula (I), supra, wherein $R^{5b}$ represents —C(=O)N$R^8R^7$; in which $R^7$ and $R^8$ together with the N atom they are attached to represent a 4- to 6-membered heterocycloalkyl-group, which is optionally substituted, one or more times, identically or differently, with a halogen atom, a $C_1$-$C_3$-alkyl- or a halo-$C_1$-$C_3$-alkyl-group.

In another preferred embodiment, the invention relates to compounds of formula (I), supra, wherein $R^6$ represents a group selected from: —$(CH_2)_q$-aryl, —$(CH_2)_q$—($C_3$-$C_6$-cycloalkyl); wherein said group is optionally substituted, one or more times, identically or differently, with a substituent selected from: halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$.

In another preferred embodiment, the invention relates to compounds of formula (I), supra, wherein $R^6$ represents a group selected from: —$(CH_2)_q$-aryl, —$(CH_2)_q$-heteroaryl, —$(CH_2)_q$—($C_3$-$C_6$-cycloalkyl), —$(CH_2)_q$-(3- to 10-membered heterocycloalkyl); wherein said group is optionally substituted, one or more times, identically or differently, with a substituent selected from: halo-, hydroxy-, cyano-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, —C(=O)$R^8$, —C(=O)O—$R^8$, —OC(=O)—$R^8$, —N(H)C(=O)$R^8$, —N($R^7$)C(=O)$R^8$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$.

In another preferred embodiment, the invention relates to compounds of formula (I), supra, wherein $R^6$ represents a group selected from: —(CH$_2$)$_q$-phenyl, —(CH$_2$)$_q$—(C$_3$-C$_6$-cycloalkyl); wherein q=1; wherein said group is optionally substituted, one or more times, identically or differently, with a substituent selected from: halo-, hydroxy-, cyano-, C$_1$-C$_3$-alkyl-, halo-C$_1$-C$_3$-alkyl-, C$_1$-C$_3$-alkoxy-, halo-C$_1$-C$_3$-alkoxy-, hydroxy-C$_1$-C$_3$-alkyl-, C$_1$-C$_3$-alkoxy-C$_1$-C$_3$-alkyl-, —C(=O)R$^8$, —C(=O)O—R$^8$, —OC(=O)—R$^8$, —N(H)C(=O)R$^8$, —N(R$^7$)C(=O)R$^8$, —NR$^8$R$^7$, —C(=O)N(H)R$^8$, —C(=O)NR$^8$R$^7$, R$^8$—S—, R$^8$—S(=O)—, R$^8$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, —N=S(=O)(R$^8$)R$^7$.

In another preferred embodiment, the invention relates to compounds of formula (I), supra, wherein R$^6$ represents a group selected from:
—(CH$_2$)$_q$-phenyl, —(CH$_2$)$_q$—(C$_3$-C$_6$-cycloalkyl); wherein said group is optionally substituted with a halogen atom.

In another preferred embodiment, the invention relates to compounds of formula (I), supra, wherein R$^6$ represents a group selected from:
—(CH$_2$)$_q$-phenyl, —(CH$_2$)$_q$—(C$_3$-C$_6$-cycloalkyl); wherein said group is optionally substituted with a group selected from a halogen atom and a methyl-group.

In another preferred embodiment, the invention relates to compounds of formula (I), wherein R$^6$ represents a group selected from:
—(CH$_2$)-phenyl, —(CH$_2$)-cyclopropyl; wherein said group is optionally substituted, one or more times, identically or differently, with a substituent selected from: halo-, C$_1$-C$_6$-alkyl-.

In another preferred embodiment, the invention relates to compounds of formula (I), wherein R$^6$ represents a group selected from:

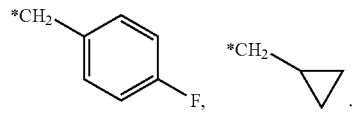

In another preferred embodiment, the invention relates to compounds of formula (I), supra, wherein R$^7$ represents a C$_1$-C$_3$-alkyl-group.

In another preferred embodiment, the invention relates to compounds of formula (I), supra, wherein R$^7$ represents a methyl-group.

In another preferred embodiment, the invention relates to compounds of formula (I), supra, wherein R$^7$ represents a C$_1$-C$_6$-alkyl-group, wherein said C$_1$-C$_6$-alkyl-group is optionally substituted, one or more times, with a halogen atom.

In another preferred embodiment, the invention relates to compounds of formula (I), supra, wherein R$^8$ represents a C$_1$-C$_3$-alkyl-group, wherein said C$_1$-C$_3$-alkyl-group is optionally substituted, one or more times, with a halogen atom.

In another preferred embodiment, the invention relates to compounds of formula (I), supra, wherein R$^9$ represents a group selected from: C$_1$-C$_3$-alkyl-, hydroxy-C$_1$-C$_3$-alkyl-, —N(H)R$^8$, N(H)(R$^8$)—C$_1$-C$_3$-alkyl-.

In another preferred embodiment, the invention relates to compounds of formula (I), supra, wherein R$^9$ represents a group selected from: C$_1$-C$_3$-alkyl-, hydroxy-C$_1$-C$_3$-alkyl-, —N(R$^{10}$)R$^{10}$, —C$_1$-C$_2$-alkyl-N(R$^{10}$)R$^{10}$; in which R$^{10}$ represents a hydrogen atom or a methyl-group.

In another preferred embodiment, the invention relates to compounds of formula (I), supra, wherein R$^9$ represents a group selected from: methyl-, hydroxy-C$_1$-C$_2$-alkyl-, —N(R$^{10}$)R$^{10}$, —C$_1$-C$_2$-alkyl-N(R$^{10}$)R$^{10}$; in which R$^{10}$ represents a hydrogen atom or a methyl-group.

In another preferred embodiment, the invention relates to compounds of formula (I), supra, wherein R$^9$ represents a group selected from: methyl-, HO—CH$_2$—, H$_2$N—CH$_2$—, —NH$_2$.

In another preferred embodiment, the invention relates to compounds of formula (I), supra, wherein R$^9$ represents a group selected from: methyl-, HO—CH$_2$—, —NH$_2$.

In another preferred embodiment, the invention relates to compounds of formula (I), supra, wherein R$^9$ represents a methyl-group.

In another preferred embodiment, the invention relates to compounds of formula (I), supra, wherein R$^9$ represents a HO—CH$_2$— group.

In another preferred embodiment, the invention relates to compounds of formula (I), supra, wherein R$^9$ represents a —NH$_2$ group.

In another preferred embodiment, the invention relates to compounds of formula (I), wherein n represents an integer of 0, 1 or 2. Preferably, n represent 0 or 1.

In another preferred embodiment, the invention relates to compounds of formula (I), wherein q represents an integer of 0, 1 or 2. Preferably, q represents 1 or 2. More preferably, q=1.

In another preferred embodiment, the invention relates to compounds of formula (I), wherein z represents an integer of 1.

In another preferred embodiment, the invention relates to compounds of formula (I), wherein z represents an integer of 2.

It is to be understood that the present invention relates also to any combination of the preferred embodiments described above.

Some examples of combinations are given hereinafter. However, the invention is not limited to these combinations.

In a preferred embodiment, the invention relates to compounds of formula (I)

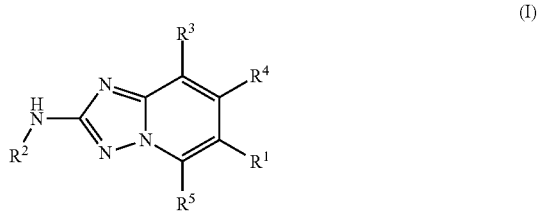

in which:
R$^1$ represents a group selected from:

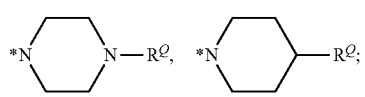

wherein * indicates the point of attachment of said group with the rest of the molecule;

$R^Q$ represents a group selected from:
—N(H)C(=O)R$^6$, —N(H)C(=O)N(H)R$^6$, —C(=O)N(H)R$^6$;

$R^2$ represents a phenyl- or pyridyl-group which is substituted one or more times, identically or differently, with a substituent selected from $R^{5a}$ and $R^{5b}$;

$R^3$ represents a hydrogen atom;
$R^4$ represents a hydrogen atom;
$R^5$ represents a hydrogen atom;
$R^{5a}$ represents a group selected from:
cyano-, $C_1$-$C_6$-alkoxy-, halo-$C_1$-$C_6$-alkoxy-, $C_1$-$C_6$-alkoxy-$C_1$-$C_6$-alkyl-, ($C_3$-$C_4$-cycloalkyl)-CH$_2$—O—;

$R^{5b}$ represents a group selected from:
—NR$^8$R$^7$, —C(=O)N(H)R$^8$, —C(=O)NR$^8$R$^7$;

$R^6$ represents a group selected from:
—CH$_2$-phenyl, —CH$_2$—(C$_3$-C$_6$-cycloalkyl);
wherein said group is optionally substituted, one or more times, identically or differently, with a substituent selected from:
halo-, $C_1$-$C_3$-alkyl-, halo-$C_1$-$C_3$-alkyl-, $C_1$-$C_3$-alkoxy-, halo-$C_1$-$C_3$-alkoxy-;

$R^7$ represents a $C_1$-$C_3$-alkyl-group;
$R^8$ represents a $C_1$-$C_6$-alkyl-group;
wherein said $C_1$-$C_6$-alkyl-group is optionally substituted, one or more times, identically or differently, with a substituent selected from:
halo-, hydroxy-, —NHR$^7$, —NR$^7$R$^7$, —N(C$_1$-C$_3$-alkyl)-C(=O)R$^7$, —N(C$_1$-C$_3$-alkyl)-C(=O)OR$^7$, $C_1$-$C_3$-alkyl-, $R^7$—S(=O)$_2$—, $C_1$-$C_3$-alkoxy-, halo-$C_1$-$C_3$-alkoxy-;
or
$R^7$ and $R^8$ together with the molecular fragment they are attached to represent a 4- to 6-membered heterocycloalkyl-group, which is optionally substituted, one or more times, identically or differently, with a halogen atom, a $C_1$-$C_3$-alkyl-, halo-$C_1$-$C_3$-alkyl- or $C_1$-$C_3$-alkoxy-group;

or a stereoisomer, a tautomer, an N-oxide, a hydrate, a solvate, or a salt thereof, or a mixture of same.

In another preferred embodiment, the invention relates to compounds of formula (I)

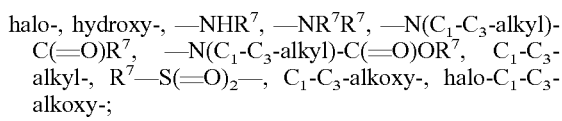
(I)

in which:
$R^1$ represents a group selected from:

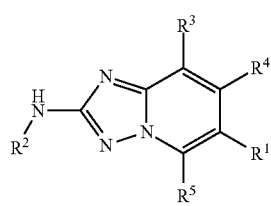

wherein * indicates the point of attachment of said group with the rest of the molecule;

$R^Q$ represents a group selected from:
—N(H)C(=O)R$^6$, —N(H)C(=O)N(H)R$^6$, —C(=O)N(H)R$^6$;

$R^2$ represents a group selected from:

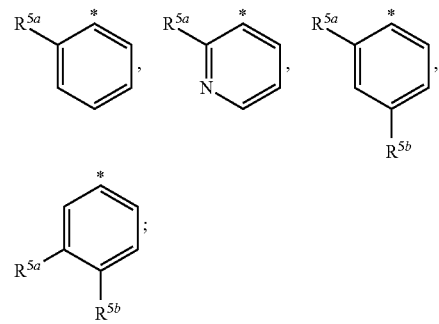

wherein * indicates the point of attachment of said group with the rest of the molecule;
$R^3$ represents a hydrogen atom;
$R^4$ represents a hydrogen atom;
$R^5$ represents a hydrogen atom;
$R^{5a}$ represents a group selected from:
cyano-, $C_1$-$C_3$-alkoxy-, halo-$C_1$-$C_3$-alkoxy-, $C_1$-$C_3$-alkoxy-$C_1$-$C_3$-alkyl-, ($C_3$-$C_4$-cycloalkyl)-CH$_2$—O—;

$R^{5b}$ represents a group selected from:
—NR$^8$R$^7$, —C(=O)N(H)R$^8$, —C(=O)NR$^8$R$^7$;

$R^6$ represents a group selected from:

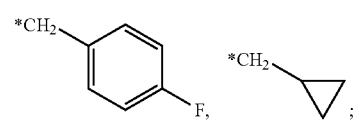

wherein * indicates the point of attachment of said group with the rest of the molecule;
$R^7$ represents a $C_1$-$C_3$-alkyl-group;
$R^8$ represents a $C_1$-$C_3$-alkyl-group;
or
$R^7$ and $R^8$ together with the molecular fragment they are attached to represent a 4- to 6-membered heterocycloalkyl-group, which is optionally substituted with a $C_1$-$C_3$-alkyl-group;

or a stereoisomer, a tautomer, an N-oxide, a hydrate, a solvate, or a salt thereof, or a mixture of same.

In another preferred embodiment, the invention relates to compounds of formula (I)

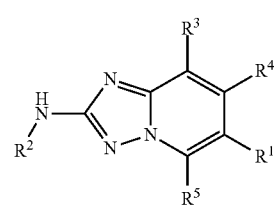
(I)

in which:
$R^1$ represents a group selected from:

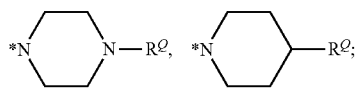

wherein * indicates the point of attachment of said group with the rest of the molecule;
$R^Q$ represents a group selected from:
—N(H)C(=O)R$^6$, —N(H)C(=O)N(H)R$^6$, —C(=O)N(H)R$^6$;
$R^2$ represents a group selected from:

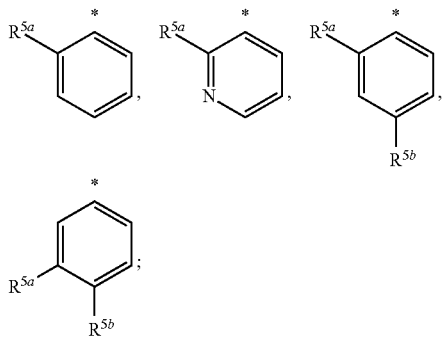

wherein * indicates the point of attachment of said group with the rest of the molecule;
$R^3$ represents a hydrogen atom;
$R^4$ represents a hydrogen atom;
$R^5$ represents a hydrogen atom;
$R^{5a}$ represents a group selected from:
—CN, methoxy-, ethoxy-, n-propoxy-, (H$_3$C)$_2$C(H)—CH$_2$—O—, cyclopropyl-CH$_2$—O—, CH$_3$—O—CH$_2$CH$_2$—O—, CF$_3$CH$_2$—O—;

$R^{5b}$ represents a group selected from:
—NR$^8$R$^7$, —C(=O)N(H)R$^8$, —C(=O)NR$^8$R$^7$;
$R^6$ represents a group selected from:

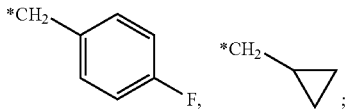

wherein * indicates the point of attachment of said group with the rest of the molecule;
$R^7$ represents a C$_1$-C$_3$-alkyl-group;
$R^8$ represents a C$_1$-C$_3$-alkyl-group;
or
$R^7$ and $R^8$ together with the molecular fragment they are attached to represent a 4- to 6-membered heterocycloalkyl-group, which is optionally substituted with a C$_1$-C$_3$-alkyl-group;
or a stereoisomer, a tautomer, an N-oxide, a hydrate, a solvate, or a salt thereof, or a mixture of same.

It is to be understood that the present invention relates to any sub-combination within any embodiment of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

EXPERIMENTAL SECTION

The following Table lists the abbreviations used in this paragraph, and in the examples section. NMR peak forms are stated as they appear in the spectra, possible higher order effects have not been considered.

| Abbreviation | Meaning |
| --- | --- |
| Ac | acetyl |
| BINAP | 2,2'-bis(diphenylphosphino)-1,1'-binaphthyl |
| Boc | tert-butyloxycarbonyl |
| br | broad |
| Brett-Phos | 2-(dicyclohexylphosphino)-3,6-dimethoxy-2'-4'-6'-tri-i-propyl-1,1'-biphenyl |
| BuPAd$_2$ | Di(1-adamantyl)-n-butylphosphine |
| c- | cyclo- |
| D/d | doublet |
| Dd/dd | doublet of doublets |
| DCM | dichloromethane |
| DMAP | N,N-dimethylpyridin-4-amine |
| DME | 1,2-dimethoxyethane |
| DIPE | diisopropylether |
| DIPEA/DIEA | N,N-diisopropylethylamine |
| DMF | N,N-dimethylformamide |
| DMSO | dimethyl sulfoxide |
| Dppf | 1,1'-bis(diphenylphosphino)ferrocene |
| Eq | equivalent |
| ESI | electrospray ionisation |
| h/hrs | hour/hours |
| HATU | N-[(dimethylamino)(3H-[1,2,3]triazolo[4,5-b]pyridin-3-yloxy)-ethylene]-N-methylmethanaminium hexafluorophosphate |
| Hünig Base | N,N-diisopropylethylamine |
| LiHMDS | lithium bis(trimethylsilyl)amide (alternative name: lithium hexamethyldisilazide) |
| M/m | multiplet |
| m.p. | melting point in ° C. |
| MS | mass spectrometry |

| Abbreviation | Meaning |
|---|---|
| MW | molecular weight |
| NaOtBu | sodium tert-butoxide; sodium 2-methylpropan-2-olate |
| NMP | N-methylpyrrolidinone |
| NMR | nuclear magnetic resonance spectroscopy: chemical shifts (δ) are given in ppm. |
| P(tBu)$_3$ | Tri-tert-butylphosphine |
| PdCl$_2$(PPh$_3$)2 | dichlorobis(triphenylphosphine)palladium(II) |
| Pd(dba)$_2$ | bis-(dibenzylideneacetone)palladium(0) complex |
| Pd$_2$(dba)$_3$ | tris-(dibenzylideneacetone)dipalladium(0) chloroform complex |
| Pd(dppf)Cl$_2$ | dichloro[1,1'-bis(diphenylphosphino)ferrocene]palladium(II) |
| Pd(dppf)Cl$_2$•CH$_2$Cl$_2$ | dichloro[1,1'-bis(diphenylphosphino)ferrocene]palladium(II) dichloromethane adduct |
| Pd-Brett-Phos-pre-cat | chloro[2-(dicyclohexylphosphino)-3,6-dimethoxy-2'-4'-6'-tri-isopropyl-1,1'-biphenyl][2-(2-aminoethyl)phenyl]palladium(II) |
| Pd-tBu—X-Phos-pre-cat | chloro(2-di-tert-butylphosphino-2',4',6'-tri-isopropyl-1,1'-biphenyl)[2-(2-aminoethyl)phenyl] palladium(II), |
| Pd—X-Phos-pre-cat | chloro(2-dicyclohexylphosphino-2',4',6'-tri-isopropyl-1,1'-biphenyl)[2-(2-aminoethyl)phenyl] palladium(II) methyl-tert-butylether adduct |
| PPh$_3$ | triphenylphosphine |
| P(oTol)$_3$ | tri-o-tolylphosphine |
| q | quartet |
| Quin/quin | quintett |
| Rac | racemic |
| Rt/r.t. | room temperature |
| RT | retention time in minutes |
| s | singlet |
| sept | septet |
| t | triplet |
| TBAF | tetrabutylammoniumfluoride |
| tBu—X-Phos | 2-di-tert-butylphosphino-2',4',6'-tri-isopropyl-1,1'-biphenyl |
| TBDPS | tert-butyldiphenylsilyl |
| TBTU | N-[(1H-benzotriazol-1-yloxy)(dimethylamino)methylene]-N-methylmethanaminium tetrafluoroborate |
| TEA | triethylamine |
| TFA | trifluoroacetic acid |
| THF | tetrahydrofuran |
| TMS | trimethylsilyl |
| Ts | para toluenesulfonyl; (tosyl) |
| UPLC | ultra performance liquid chromatography |
| X-Phos | 2-dicyclohexylphosphino-2',4',6'-triisopropylbiphenyl |

Methods for the preparation of substituted [1,2,4]-triazolo-[1,5-a]-pyridines are described e.g. in WO 2011/064328 A1, WO 2011/063907 A1, WO 2011/063908 A1, WO 2012/143329 A1, WO 2013/087579 A1 and WO 2014/009219 A1.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "×HCl", "×CF$_3$COOH", "×Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

General Procedures

General Procedure 1A

The [1,2,4]triazolo[1,5-a]pyridin-2-amine containing building block (1 eq.), the halogenarene (1.2 eq.), chloro(2-dicyclohexylphosphino-2',4',6'-tri-isopropyl-1,1'-biphenyl)[2-(2-aminoethyl)phenyl] palladium(II) methyl-tert-butylether adduct (0.04 eq.), 2-dicyclohexylphosphino-2',4',6'-triisopropylbiphenyl (0.04 eq.) and sodium tert-butoxide (2.4 eq.) were pre-mixed in an argon atmosphere. Degassed toluene (7-10 mL/mmol amine) was added, and the mixture was put in a pre-heated oil bath of 100-130° C. and stirred at this temperature until consumption of the amine (typically 2-20 h). The mixture was then diluted with satd. sodium carbonate solution and extracted with ethyl acetate. The organic layer was dried over sodium sulphate, and the solvent was evaporated to yield a crude product which was purified by column chromatography on silica gel or by preparative HPLC.

General Procedure 1B

The procedure equals general procedure 1A, but more catalyst chloro(2-dicyclohexylphosphino-2',4',6'-tri-isopropyl-1,1'-biphenyl)[2-(2-aminoethyl)-phenyl] palladium(II) methyl-tert-butylether adduct (0.1 eq.) and 2-dicyclohexylphosphino-2',4',6'-triisopropylbiphenyl (0.1 eq.) was used.

Synthesis of Intermediate Compounds

Intermediate Example Int01.01 tert-butyl 4-(6-nitropyridin-3-yl)piperazine-1-carboxylate

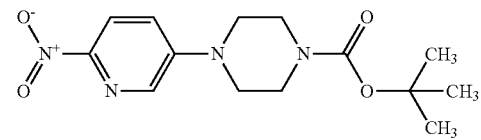

5-Bromo-2-nitropyridine (31.2 g, 154 mmol) and tert-butyl piperazine-1-carboxylate (37.2 g, 200 mmol) were dissolved in DMSO (90 mL), and triethylamine (27.8 mL, 200 mmol) was added. The mixture was stirred at 70° C. overnight, then cooled to rt and poured into water. The precipitate was collected by suction filtration, washed twice with water and tert-butyl methyl ether and dried in vacuo to yield 41.4 g (81%) of the title compound in 93% purity as yellow crystals.

$^1$H-NMR (400 MHz, DMSO-$d_6$): δ [ppm]=1.43 (s, 9H), 3.46-3.55 (m, 8H), 7.47 (dd, 1H), 8.17 (d, 1H), 8.25 (d, 1H).

Intermediate Example Int01.02 tert-butyl 4-(6-aminopyridin-3-yl)piperazine-1-carboxylate

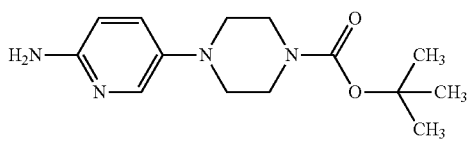 [SMILES: CC(C)(C)OC(=O)N1CCN(c2ccc(N)nc2)CC1]

Tert-butyl 4-(6-nitropyridin-3-yl)piperazine-1-carboxylate (41.3 g, 134 mmol) from example Int01.01 was dissolved in a mixture of ethanol (0.5 L) and ethyl acetate (0.5 L), and 10% palladium on charcoal (4.10 g) was added. The mixture was stirred at rt for 5 h under hydrogen atmosphere (1 bar). Subsequently, the mixture was filtered and the solvent was removed in vacuo. The residue was triturated with tert-butyl methyl ether and the product collected by suction filtration to yield 26.0 g (69%) of the title compound. The mother liquor was purified by column chromatography on silica gel (eluent: gradient 100% ethyl acetate to ethyl acetate/methanol 5:1) to yield further 4.2 g (11%).

$^1$H-NMR (400 MHz, DMSO-$d_6$): δ [ppm]=1.41 (s, 9H), 2.83-2.87 (m, 4H), 3.40-3.44 (m, 4H), 5.45 (s, 2H), 6.39 (d, 1H), 7.17 (dd, 1H), 7.61 (d, 1H).

Intermediate Example Int01.03 tert-butyl 4-(6-{[(ethoxycarbonyl)carbamothioyl]amino}pyridin-3-yl)piper-azine-1-carboxylate

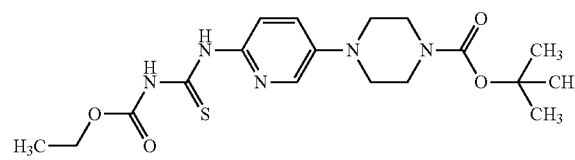

Tert-butyl 4-(6-aminopyridin-3-yl)piperazine-1-carboxylate (26.0 g, 93.2 mmol) from example Int01.02 was dissolved in dioxane (100 mL) and ethyl carbonisothiocyanatidate (12.2 g, 93.2 mmol) was slowly added at rt. The mixture was stirred for 3 h at rt and then concentrated in vacuo. The residue was triturated with tert-butyl methyl ether, and the precipitate was collected by suction filtration to yield 33.5 g (88%) of the title compound as tan crystals.

$^1$H-NMR (400 MHz, DMSO-$d_6$): δ [ppm]=1.26 (t, 3H), 1.42 (s, 9H), 3.14-3.19 (m, 4H), 3.44-3.49 (m, 4H), 4.22 (q, 2H), 7.48 (d, 1H), 8.10 (br. s, 1H), 8.49 (br. s, 1H), 11.32 (br. s., 1H), 12.01 (br. s., 1H).

Intermediate Example Int01.04 tert-butyl 4-(2-amino[1,2,4]triazolo[1,5-a]pyridin-6-yl)piperazine-1-carboxylate

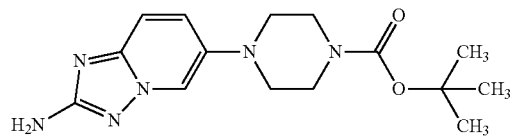

To hydroxylamine hydrochloride (37.6 g, 542 mmol) were added methanol (189 mL), ethanol (182 mL) and N,N-diisopropylethylamine (56.9 mL, 327 mmol), and the suspension was heated to 60° C. Tert-butyl 4-(6-{[(ethoxycarbonyl)carbamothioyl]amino}pyridin-3-yl)piperazine-1-carboxylate (38.2 g, 93.4 mmol) from example Int01.03 was added, and heating to 60° C. was continued for 6 h. The solvents were then evaporated, and the residue was triturated with water. The precipitate was separated, triturated with tert-butyl methyl ether, and collected by suction filtration to yield 26.6 g (89%) of the title compound as greyish crystals.

$^1$H-NMR (400 MHz, DMSO-$d_6$): δ [ppm]=1.42 (s, 9H), 2.96-3.01 (m, 4H), 3.44-3.49 (m, 4H), 5.74-5.79 (m, 2H), 7.26 (d, 1H), 7.37 (dd, 1H), 8.03 (d, 1H).

Intermediate Example Int01.05

6-(piperazin-1-yl)[1,2,4]triazolo[1,5-a]pyridin-2-amine

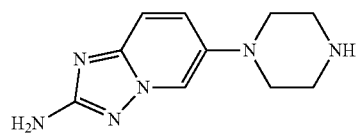 [SMILES: Nc1nc2ccc(N3CCNCC3)cn2n1]

Tert-butyl 4-(2-amino[1,2,4]triazolo[1,5-a]pyridin-6-yl)piperazine-1-carboxylate (2.00 g, 6.28 mmol) from example Int01.04 was suspended in DCM (16 mL) and TFA (4.8 mL, 63 mmol) was added at rt. Stirring was continued for 2 h. Subsequently, the mixture was concentrated in vacuo and the residue was re-dissolved in ethyl acetate/satd. sodium carbonate solution. The organic layer was separated. The aqueous layer was concentrated and the residue eluted with ethyl acetate and methanol. The combined organic layers were dried over sodium sulphate. The solvents were evaporated. Tert-butyl methyl ether and some drops of methanol were added, and the mixture was sonicated. The precipitate was collected by suction filtration to yield 1.12 g (65%) of the title compound as off-white crystals.

$^1$H-NMR (400 MHz, DMSO-$d_6$): δ [ppm]=2.80-2.85 (m, 4H), 2.90-2.96 (m, 4H), 3.41 (br. s., 1H), 5.70-5.75 (m, 2H), 7.23 (d, 1H), 7.35 (dd, 1H), 7.94 (d, 1H).

Intermediate Example Int01.06

4-(2-amino[1,2,4]triazolo[1,5-a]pyridin-6-yl)-N-(4-fluorobenzyl)piperazine-1-carboxamide

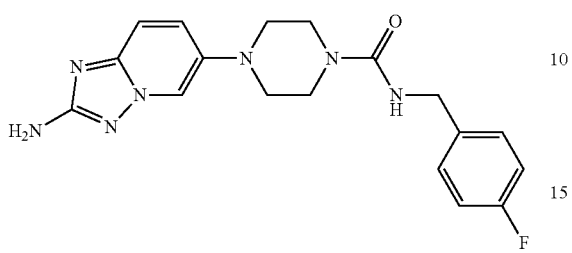

6-(Piperazin-1-yl)[1,2,4]triazolo[1,5-a]pyridin-2-amine (650 mg, 2.98 mmol) from example Int01.05 was suspended in dry THF (13 mL) and cooled to <5° C. 1-Fluoro-4-(isocyanatomethyl)benzene (495 mg, 3.28 mmol) was added, and stirring was continued for 2 h. The mixture was then concentrated in vacuo, and the residue was triturated with tert-butyl methyl ether. The precipitate was collected by suction filtration to yield 1.09 g (96%) of the title compound as off-white crystals.

$^1$H-NMR (400 MHz, DMSO-$d_6$): δ [ppm]=2.97-3.03 (m, 4H), 3.46-3.51 (m, 4H), 4.23 (d, 2H), 5.76 (s, 2H), 7.09-7.16 (m, 2H), 7.20-7.32 (m, 4H), 7.40 (dd, 1H), 8.04 (d, 1H).

Intermediate Example Int01.07 tert-butyl 4-(2-{[4-(diethylcarbamoyl)-2-methoxyphenyl]amino}[1,2,4]-triazolo[1,5-a]pyridin-6-yl)piperazine-1-carboxylate

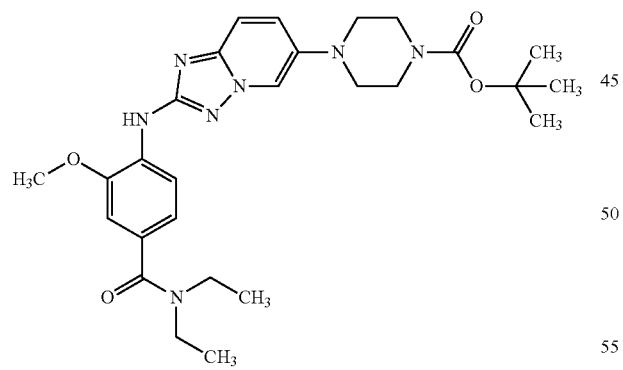

Following general procedure 1A, tert-butyl 4-(2-amino[1,2,4]triazolo[1,5-a]pyridin-6-yl)piperazine-1-carboxylate (200 mg, 0.628 mmol) from example Int01.04 was reacted with 4-bromo-N,N-diethyl-3-methoxybenzamide (216 mg, 0.754 mmol) to yield 251 mg (76%) of the title compound.

$^1$H-NMR (400 MHz, DMSO-$d_6$): δ [ppm]=1.13 (t, 6H), 1.43 (s, 9H), 3.04-3.09 (m, 4H), 3.30-3.40 (m, 4H), 3.48 (d, 4H), 3.90 (s, 3H), 6.95-6.99 (m, 2H), 7.51 (d, 1H), 7.57 (dd, 1H), 7.99 (s, 1H), 8.27 (dd, 2H).

Intermediate Example Int01.08

N,N-diethyl-3-methoxy-4-{[6-(piperazin-1-yl)[1,2,4]triazolo[1,5-a]pyridin-2-yl]amino}benzamide

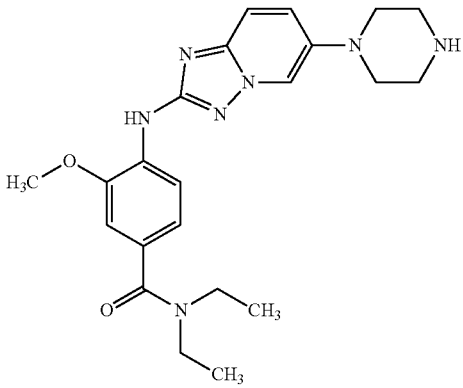 [SMILES: CCN(CC)C(=O)c1ccc(Nc2nc3ccc(N4CCNCC4)cn3n2)c(OC)c1]

Tert-butyl 4-(2-{[4-(diethylcarbamoyl)-2-methoxyphenyl]amino}[1,2,4]triazolo-[1,5-a]pyridin-6-yl)piperazine-1-carboxylate (358 mg, 0.684 mmol) from example Int01.07 was added to ice-cold 4N hydrochloric acid in dioxane (5.0 mL), and the mixture was slowly warmed to rt. After stirring for 3 h, the mixture was poured into satd. sodium carbonate solution and extracted with ethyl acetate. The organic layer was dried over sodium sulphate, and the solvent was evaporated to yield 241 mg (83%) of the title compound.

$^1$H-NMR (400 MHz, DMSO-$d_6$): δ [ppm]=1.13 (t, 6H), 2.83-2.88 (m, 4H), 2.99-3.03 (m, 4H), 3.32-3.39 (m, 4H), 3.90 (s, 3H), 6.95-6.99 (m, 2H), 7.48 (d, 1H), 7.55 (dd, 1H), 7.95 (s, 1H), 8.18 (d, 1H), 8.28 (d, 1H).

Intermediate Example Int02.01

Ethyl 1-(6-nitropyridin-3-yl)piperidine-4-carboxylate

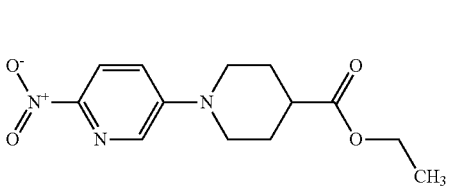 [SMILES: CCOC(=O)C1CCN(c2ccc([N+](=O)[O-])nc2)CC1]

5-Bromo-2-nitropyridine (10.0 g, 49.3 mmol) and ethyl piperidine-4-carboxylate (10.1 g, 64.0 mmol) were dissolved in DMSO (30 mL), and triethylamine (8.93 mL, 64.0 mmol) was added. The mixture was stirred at 70° C. overnight, then cooled to rt and poured into water. The mixture was extracted with tert-butyl methyl ether. The organic layer was dried over sodium sulphate, and the solvent was evaporated. The residue was purified by column chromatography on silica gel (eluent: cyclohexane/ethyl acetate 1:1), and the product was triturated with tert-butyl methyl ether and collected by suction filtration to yield 6.02 g (44%) of the title compound as yellow crystals.

$^1$H-NMR (400 MHz, DMSO-$d_6$): δ [ppm]=1.19 (t, 3H), 1.56-1.68 (m, 2H), 1.89-1.97 (m, 2H), 2.68 (tt, 1H), 3.10-3.19 (m, 2H), 3.98-4.05 (m, 2H), 4.08 (q, 2H), 7.48 (dd, 1H), 8.13 (d, 1H), 8.25 (d, 1H).

Intermediate Example Int02.02 ethyl 1-(6-aminopyridin-3-yl)piperidine-4-carboxylate

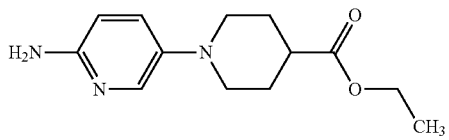

Ethyl 1-(6-nitropyridin-3-yl)piperidine-4-carboxylate (6.00 g, 21.5 mmol) from example Int02.01 was dissolved in a 1:1 mixture of ethanol and ethyl acetate (100 mL each), and 10% palladium on charcoal (600 mg) was added. The mixture was stirred for 4 h at rt under a hydrogen atmosphere (1 bar). Subsequently, the mixture was filtered and the solvent was removed in vacuo. The residue was triturated with tert-butyl methyl ether and the product collected by suction filtration to yield 5.19 g (97%) of the title.

$^1$H-NMR (400 MHz, DMSO-d$_6$): δ [ppm]=1.19 (t, 3H), 1.61-1.72 (m, 2H), 1.85-1.93 (m, 2H), 2.39 (tt, 1H), 2.58 (td, 2H), 3.28 (dt, 2H), 4.08 (q, 2H), 5.36-5.41 (m, 2H), 6.38 (d, 1H), 7.15 (dd, 1H), 7.60 (d, 1H).

Intermediate Example Int02.03 ethyl 1-(6-{[(ethoxycarbonyl)carbamothioyl]amino}pyridin-3-yl)piperidine-4-carboxylate

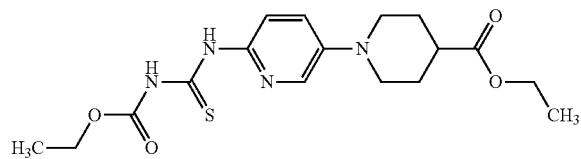

Ethyl 1-(6-aminopyridin-3-yl)piperidine-4-carboxylate (4.43 g, 17.8 mmol) from example Int02.02 was dissolved in dioxane (50 mL) and ethyl carbonisothiocyanatidate (2.33 g, 17.8 mmol) was slowly added at rt. The mixture was stirred at rt for 3 h and then concentrated in vacuo. The residue was triturated with tert-butyl methyl ether, and the precipitate was collected by suction filtration to yield 6.60 g (98%) of the title compound as tan crystals.

$^1$H-NMR (400 MHz, DMSO-d$_6$): δ [ppm]=1.19 (t, 3H), 1.26 (t, 3H), 1.59-1.71 (m, 2H), 1.91 (dd, 2H), 2.52-2.53 (m, 1H), 2.83 (td, 2H), 3.68 (d, 2H), 4.08 (q, 2H), 4.21 (q, 2H), 7.42-7.49 (m, 1H), 8.09 (br. s., 1H), 8.42-8.51 (m, 1H), 11.30 (br. s., 1H), 11.99 (br. s., 1H).

Intermediate Example Int02.04

Ethyl 1-(2-amino[1,2,4]triazolo[1,5-a]pyridin-6-yl)piperidine-4-carboxylate

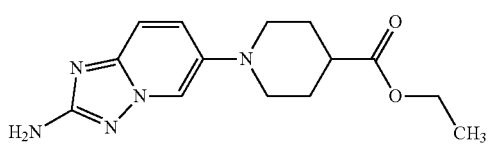

To hydroxylamine hydrochloride (8.19 g, 118 mmol) was added methanol (41.2 mL), ethanol (39.6 mL) and N,N-diisopropylethylamine (12.4 mL, 71.2 mmol), and the suspension was heated to 60° C. Ethyl 1-(6-{[(ethoxycarbonyl)carbamothioyl]amino}pyridin-3-yl)piperidine-4-carboxylate (7.74 g, 20.3 mmol) from example Int02.03 was added, and heating to 60° C. was continued for 6 h. The solvents were then evaporated, and the residue was taken up in ethyl acetate. The solution was washed with water, dried over sodium sulphate and concentrated in vacuo. The residue was crystallized from tert-butyl methyl ether to yield 4.24 g (70%) of the title compound.

$^1$H-NMR (400 MHz, DMSO-d$_6$): δ [ppm]=1.20 (t, 3H), 1.64-1.76 (m, 2H), 1.89-1.97 (m, 2H), 2.46 (qq, 1H), 2.68 (td, 2H), 3.45 (dt, 2H), 4.09 (q, 2H), 5.72-5.76 (m, 2H), 7.23 (d, 1H), 7.36 (dd, 1H), 7.99 (d, 1H).

Intermediate Example Int02.05

1-(2-amino[1,2,4]triazolo[1,5-a]pyridin-6-yl)-N-(4-fluorobenzyl)piperidine-4-carboxamide

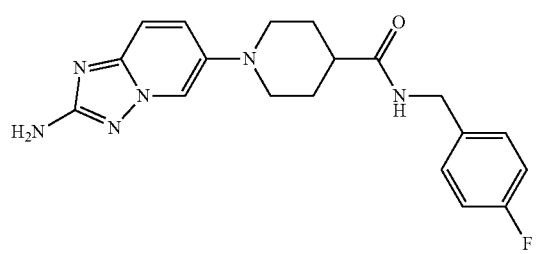 [SMILES: Nc1nc2ccc(N3CCC(C(=O)NCc4ccc(F)cc4)CC3)cn2n1]

Ethyl 1-(2-amino[1,2,4]triazolo[1,5-a]pyridin-6-yl)piperidine-4-carboxylate (200 mg, 0.69 mmol) from example Int02.04 was dissolved in 1-(4-fluorophenyl)methanamine (3.31 g, 26.4 mmol), and magnesium chloride (33 mg, 0.35 mmol) was added. The mixture was heated in a microwave oven for 1 h to 200° C. Subsequently, it was diluted with ethyl acetate, washed with satd. ammonium chloride solution, dried over sodium sulphate and evaporated. The crude product was purified by column chromatography on silica gel (eluent: ethyl acetate/methanol 5:1) to yield 73 mg (26%) of the title compound.

$^1$H-NMR (400 MHz, DMSO-d$_6$): δ [ppm]=1.67-1.86 (m, 4H), 2.30 (tt, 1H), 2.60 (td, 2H), 3.50-3.56 (m, 2H), 4.26 (d, 2H), 5.71-5.74 (m, 2H), 7.11-7.18 (m, 2H), 7.22 (d, 1H), 7.25-7.30 (m, 2H), 7.36 (dd, 1H), 7.99 (d, 1H), 8.38 (t, 1H).

Intermediate Example Int02.06

1-(2-amino[1,2,4]triazolo[1,5-a]pyridin-6-yl)-N-(cyclopropylmethyl)-piperidine-4-carboxamide

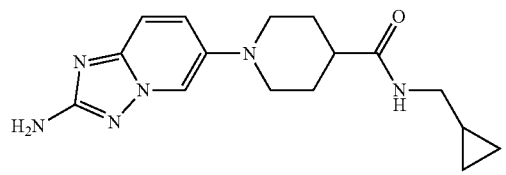 [SMILES: Nc1nc2ccc(N3CCC(C(=O)NCC4CC4)CC3)cn2n1]

Ethyl 1-(2-amino[1,2,4]triazolo[1,5-a]pyridin-6-yl)piperidine-4-carboxylate (500 mg, 1.73 mmol) from example Int02.04 was dissolved in 1-cyclopropylmethanamine (2.46 g, 34.6 mmol). One drop of 1-butyl-3-methyl-imidazolium tetrafluoroborate was added, and the mixture was heated in a microwave oven for 6 h to 200° C. Subsequently, the mixture was concentrated in vacuo. The crude product was purified by column chromatography on silica gel (eluent: ethyl acetate/methanol 5:1) to yield 364 mg (67%) of the title compound.

¹H-NMR (400 MHz, DMSO-$d_6$): δ [ppm]=0.11-0.17 (m, 2H), 0.36-0.42 (m, 2H), 0.83-0.94 (m, 1H), 1.64-1.81 (m, 4H), 2.23 (tt, 1H), 2.55-2.62 (m, 2H), 2.95 (t, 2H), 3.48-3.56 (m, 2H), 5.71-5.75 (m, 2H), 7.22 (d, 1H), 7.36 (dd, 1H), 7.89 (t, 1H), 7.99 (d, 1H).

Intermediate Example Int03.01 tert-butyl[1-(6-nitropyridin-3-yl)piperidin-4-yl]carbamate

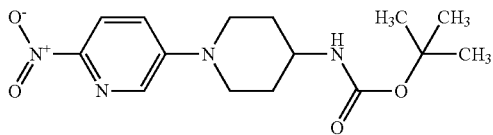

5-Bromo-2-nitropyridine (5.00 g, 24.6 mmol) and tert-butyl piperidin-4-ylcarbamate (6.41 g, 32.0 mmol) were dissolved in DMSO (15 mL), and triethylamine (4.46 mL, 32.0 mmol) was added. The mixture was stirred at 70° C. overnight, then cooled to rt and poured into water. The precipitate was collected by suction filtration and purified by column chromatography on silica gel (eluent (cyclohexane/ethyl acetate 1:1) to yield 6.26 g (64%) of the title compound as yellow solid.

¹H-NMR (400 MHz, DMSO-$d_6$): δ [ppm]=1.35-1.46 (m, 2H), 1.39 (s, 9H), 1.82 (d, 2H), 3.06-3.15 (m, 2H), 3.50-3.63 (m, 1H), 4.01 (dt, 2H), 6.90 (d, 1H), 7.46 (dd, 1H), 8.13 (d, 1H), 8.24 (d, 1H).

Intermediate Example Int03.02 tert-butyl[1-(6-aminopyridin-3-yl)piperidin-4-yl]carbamate

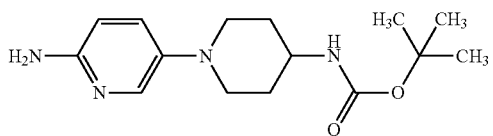 [SMILES: CC(C)(C)OC(=O)NC1CCN(c2ccc(N)nc2)CC1]

Tert-butyl [1-(6-nitropyridin-3-yl)piperidin-4-yl]carbamate (6.26 g, 19.4 mmol) from example Int03.01 was dissolved in a mixture of ethanol (100 mL), ethyl acetate (100 mL), and DME (100 mL), and 10% palladium on charcoal (1.94 g) was added. The mixture was stirred overnight at rt under hydrogen atmosphere (1 bar). Subsequently, the mixture was filtered and the solvent was removed in vacuo. The residue was triturated with tert-butyl methyl ether and the product collected by suction filtration to yield 5.37 g (86%) of the title compound in 91% purity as tan crystals.

¹H-NMR (400 MHz, DMSO-$d_6$): δ [ppm]=1.39 (s, 9H), 1.41-1.55 (m, 2H), 1.73-1.80 (m, 2H), 2.51-2.58 (m, 2H), 3.23-3.30 (m, 3H), 5.34-5.38 (m, 2H), 6.37 (d, 1H), 6.83 (d, 1H), 7.14 (dd, 1H), 7.59 (d, 1H).

Intermediate Example Int03.03 ethyl[(5-{4-[(tert-butoxycarbonyl)amino]piperidin-1-yl}pyridin-2-yl)carbamothioyl]carbamate

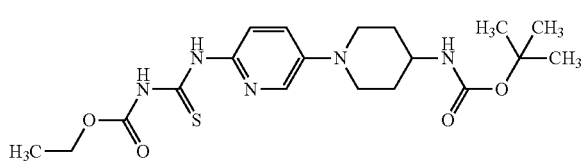 [SMILES: CCOC(=O)NC(=S)Nc1ccc(N2CCC(NC(=O)OC(C)(C)C)CC2)cn1]

Tert-butyl [1-(6-aminopyridin-3-yl)piperidin-4-yl]carbamate (5.37 g, 18.4 mmol) from example Int03.02 was dissolved in dioxane (69 mL) and ethyl carbonisothiocyanatidate (2.41 g, 18.4 mmol) was slowly added at rt. The mixture was stirred at rt overnight and then concentrated in vacuo. The residue was triturated with tert-butyl methyl ether, and the precipitate was collected by suction filtration to yield 8.37 g (95%) of the title compound in 88% purity.

¹H-NMR (400 MHz, DMSO-$d_6$): δ [ppm]=1.26 (t, 3H), 1.39 (s, 9H), 1.38-1.55 (m, 2H), 1.76-1.83 (m, 2H), 2.74-2.84 (m, 2H), 3.36-3.47 (m, 1H), 3.65-3.73 (m, 2H), 4.21 (q, 2H), 6.86 (d, 1H), 7.41-7.48 (m, 1H), 8.05-8.10 (m, 1H), 8.40-8.49 (m, 1H).

Intermediate Example Int03.04 tert-butyl[1-(2-amino[1,2,4]triazolo[1,5-a]pyridin-6-yl)piperidin-4-yl]-carbamate

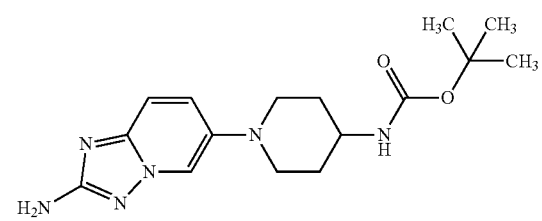

To hydroxylamine hydrochloride (7.97 g, 115 mmol) was added methanol (40.0 mL), ethanol (38.5 mL) and N,N-diisopropylethylamine (12.0 mL, 69.2 mmol), and the suspension was heated to 60° C. Ethyl [(5-{4-[(tert-butoxycarbonyl)amino]piperidin-1-yl}pyridin-2-yl)carbamothioyl]carbamate (8.37 g, 19.8 mmol) from example Int03.03 was added, and heating to 60° C. was continued for 3 h. The solvents were then evaporated, and the residue was triturated with water. The precipitate was separated, triturated twice with tert-butyl methyl ether, and collected by suction filtration. 4.50 g (64%) of the title compound was isolated.

¹H-NMR (400 MHz, DMSO-$d_6$): δ [ppm]=1.39 (s, 9H), 1.51 (dd, 2H), 1.77-1.85 (m, 2H), 2.60-2.69 (m, 2H), 3.33-3.39 (m, 1H), 3.40-3.47 (m, 2H), 5.71-5.75 (m, 2H), 6.87 (d, 1H), 7.21 (d, 1H), 7.35 (dd, 1H), 7.97 (d, 1H).

Intermediate Example Int03.05

6-(4-aminopiperidin-1-yl)[1,2,4]triazolo[1,5-a]pyridin-2-amine hydrochloride

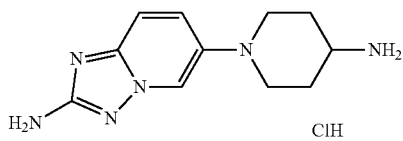 [SMILES: Nc1nc2ccc(N3CCC(N)CC3)cn2n1 ; Cl]

Tert-butyl [1-(2-amino[1,2,4]triazolo[1,5-a]pyridin-6-yl)piperidin-4-yl]carbamate (3.00 g, 8.41 mmol) from example Int03.04 was suspended in dioxane (30 mL) and hydrochloric acid (4N in dioxane, 6.3 mL) was added at rt. Stirring was continued for 3 h. Subsequently, the mixture was concentrated in vacuo and the residue was triturated with tert-butyl methyl ether. The precipitate was collected by suction filtration to yield 3.40 g of the title compound as off-white crystals.

$^1$H-NMR (400 MHz, DMSO-$d_6$): δ [ppm]=1.69 (qd, 2H), 1.97-2.07 (m, 2H), 2.84 (t, 2H), 3.14-3.27 (m, 1H), 3.75 (d, 2H), 7.41 (br. s., 1H), 7.61 (d, 1H), 7.86 (dd, 1H), 8.34 (br. s., 2H), 8.39 (br. s., 1H), 8.43 (d, 1H).

Intermediate Example Int03.06

N-[1-(2-amino[1,2,4]triazolo[1,5-a]pyridin-6-yl)piperidin-4-yl]-2-(4-fluorophenyl)acetamide

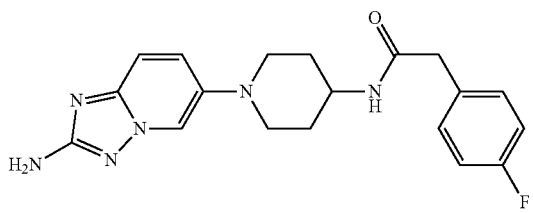 [SMILES: Nc1nc2ccc(N3CCC(NC(=O)Cc4ccc(F)cc4)CC3)cn2n1]

(4-Fluorophenyl)acetic acid (1.01 g, 6.55 mmol) was dissolved in DCM (57 mL) and DMF (40 mL) and cooled to 0° C. Oxalylchloride (914 mg, 7.20 mmol) was added, and the mixture was stirred for 10 min. 6-(4-Aminopiperidin-1-yl)[1,2,4]triazolo[1,5-a]pyridin-2-amine hydrochloride (2.00 g, 6.55 mmol) from example Int03.05 and N,N-diisopropyl ethylamine (4.56 mL, 26.2 mmol) were added, and the mixture was warmed to rt. After consumption of the starting material, the mixture was diluted with satd. sodium carbonate solution and extracted three times with ethyl acetate. The combined organic layers were washed with buffer solution (pH 2), satd. sodium bicarbonate solution and brine, dried over sodium sulphate, and the solvent was evaporated. The product was purified by preparative HPLC (Reprosil C18 10 μm 470×50: gradient water (0.5% formic acid)/methanol 70:30 to 40:60) to yield 218 mg (9%) of the title compound.

$^1$H-NMR (400 MHz, DMSO-$d_6$): δ [ppm]=1.48-1.59 (m, 2H), 1.79-1.87 (m, 2H), 2.71 (td, 2H), 3.33-3.37 (m, 1H), 3.41-3.48 (m, 2H), 3.60-3.71 (m, 1H), 5.71-5.75 (m, 2H), 7.09-7.15 (m, 2H), 7.22 (d, 1H), 7.26-7.31 (m, 2H), 7.36 (dd, 1H), 7.99 (d, 1H), 8.09 (d, 1H), 8.15 (br. s., 1H).

Intermediate Example Int04.01 tert-butyl[1-(6-nitropyridin-3-yl)pyrrolidin-3-yl]carbamate

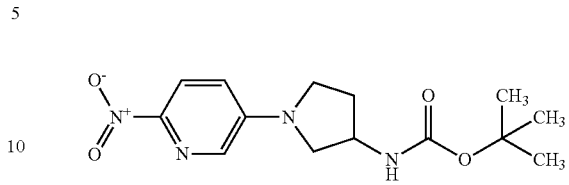

5-Bromo-2-nitropyridine (10.0 g, 49.3 mmol) and tert-butyl pyrrolidin-3-ylcarbamate (11.9 g, 64.0 mmol) were dissolved in DMSO (30 mL), and triethylamine (8.93 mL, 64.0 mmol) was added. The mixture was stirred at 70° C. for 5 h, then cooled to rt and poured into water. The mixture was extracted with ethyl acetate. The organic layer was dried over sodium sulphate, and the solvent was evaporated. The residue was triturated with ethyl acetate, and the precipitate was collected by suction filtration. The mother liquor was purified by preparative HPLC to yield a second batch. 10.5 g (69%) of the title compound were obtained.

$^1$H-NMR (400 MHz, DMSO-$d_6$): δ [ppm]=1.39 (s, 9H), 1.82-1.91 (m, 1H), 2.07-2.16 (m, 1H), 3.17 (dd, 1H), 3.29-3.37 (m, 1H), 3.42-3.50 (m, 1H), 3.55 (dd, 1H), 4.05-4.14 (m, 1H), 6.42 (d, 1H), 7.20 (d, 1H), 7.62 (dd, 1H), 8.11 (d, 1H).

Intermediate Example Int04.02 tert-butyl[1-(6-aminopyridin-3-yl)pyrrolidin-3-yl]carbamate

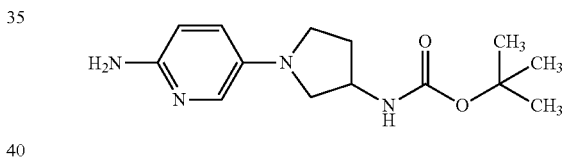

Tert-butyl [1-(6-nitropyridin-3-yl)pyrrolidin-3-yl]carbamate (8.87 g, 28.8 mmol) from example Int04.01 was dissolved in a 1:1 mixture of ethanol and ethyl acetate (130 mL each), and 10% palladium on charcoal (887 mg) was added. The mixture was stirred for 4 h at rt under hydrogen atmosphere (1 bar). Subsequently, the mixture was filtered and the solvent was removed in vacuo to yield 7.72 g (96%) of the title as grayish crystals.

$^1$H-NMR (400 MHz, DMSO-$d_6$): δ [ppm]=1.39 (s, 9H), 1.76-1.86 (m, 1H), 2.06-2.16 (m, 1H), 2.89 (dd, 1H), 3.05-3.13 (m, 1H), 3.20 (td, 1H), 3.30-3.36 (m, 1H), 4.03-4.14 (m, 1H), 5.02-5.07 (m, 2H), 6.39 (d, 1H), 6.82 (dd, 1H), 7.13 (d, 1H), 7.31 (d, 1H).

Intermediate Example Int04.03 ethyl[(5-{3-[(tert-butoxycarbonyl)amino]pyrrolidin-1-yl}pyridin-2-yl)-carbamothioyl]carbamate

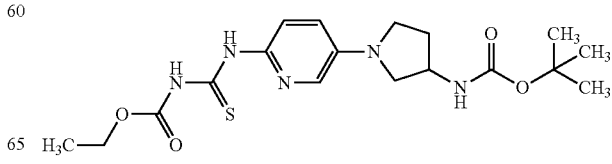

Tert-butyl [1-(6-aminopyridin-3-yl)pyrrolidin-3-yl]carbamate (7.70 g, 27.7 mmol) from example Int04.02 was dissolved in dioxane (100 mL) and ethyl carbonisothiocyanatidate (3.63 g, 27.7 mmol) was slowly added at rt. The mixture was stirred at rt overnight and then concentrated in vacuo. The residue was triturated with tert-butyl methyl ether, and the precipitate was collected by suction filtration to yield 10.4 g (92%) of the title compound as slightly olive-green crystals.

$^1$H-NMR (400 MHz, DMSO-d$_6$): δ [ppm]=1.26 (t, 3H), 1.39 (s, 9H), 1.84-1.94 (m, 1H), 2.10-2.19 (m, 1H), 3.07 (dd, 1H), 3.23-3.31 (m, 1H), 3.35-3.42 (m, 1H), 3.49 (dd, 1H), 4.12-4.18 (m, 1H), 4.21 (q, 2H), 6.97-7.03 (m, 1H), 7.22 (d, 1H), 7.69 (d, 1H), 8.34-8.40 (m, 1H), 11.22 (br. s, 1H), 11.91 (br. s., 1H).

Intermediate Example Int04.04 tert-butyl[1-(2-amino[1,2,4]triazolo[1,5-a]pyridin-6-yl)pyrrolidin-3-yl]-carbamate

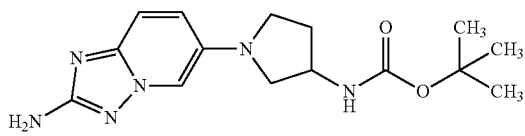 [SMILES: CC(C)(C)OC(=O)NC1CCN(c2ccc3nc(N)nn3c2)C1]

To hydroxylamine hydrochloride (10.2 g, 147 mmol) was added methanol (51.3 mL), ethanol (49.4 mL) and N,N-diisopropylethylamine (15.4 mL, 88.6 mmol), and the suspension was heated to 60° C. Ethyl [(5-{3-[(tert-butoxycarbonyl)amino]pyrrolidin-1-yl}pyridin-2-yl)carbamothioyl]carbamate (10.4 g, 25.3 mmol) from example Int04.03 was added, and heating to 60° C. was continued overnight. The solvents were then evaporated, and the residue was triturated with water. The precipitate was collected by suction filtration, triturated with tert-butyl methyl ether and collected to yield 6.90 g (86%) of the title compound.

$^1$H-NMR (400 MHz, DMSO-d$_6$): δ [ppm]=1.39 (s, 9H), 1.82-1.92 (m, 1H), 2.10-2.20 (m, 1H), 2.99 (dd, 1H), 3.15-3.23 (m, 1H), 3.26-3.32 (m, 1H), 3.43 (dd, 1H), 4.09-4.19 (m, 1H), 5.59-5.66 (m, 2H), 7.04 (dd, 1H), 7.18 (br. s., 1H), 7.21 (d, 1H), 7.68 (d, 1H).

Intermediate Example Int04.05

6-(3-aminopyrrolidin-1-yl)[1,2,4]triazolo[1,5-a]pyridin-2-amine hydrochloride

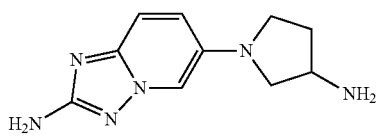

Tert-butyl [1-(2-amino[1,2,4]triazolo[1,5-a]pyridin-6-yl)pyrrolidin-3-yl]-carbamate (6.90 g, 21.7 mmol) from example Int04.04 was dissolved in DCM (56 mL) and treated with trifluoro acetic acid (16.7 mL). The mixture was stirred for 2 h at rt and was then diluted with satd. sodium carbonate solution. The aqueous layer was washed once with ethyl acetate. The organic layer was then concentrated in vacuo and the residue treated with methanol. The methanolic phase was concentrated in vacuo. The residue was treated with DCM/methanol (10:1) and the liquid phase was concentrated. The residue was treated with dioxane/THF, and 4N hydrochloric acid in dioxane was added. The mixture was concentrated in vacuo, and the residue was used without further purification.

Intermediate Example Int04.06

1-[1-(2-amino[1,2,4]triazolo[1,5-a]pyridin-6-yl)pyrrolidin-3-yl]-3-(4-fluoro-benzyl)urea

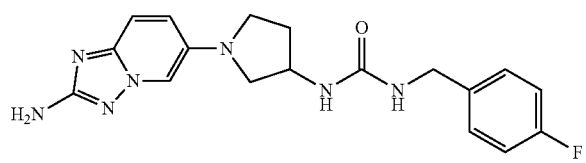 [SMILES: Nc1nc2ccc(N3CCC(NC(=O)NCc4ccc(F)cc4)C3)cn2n1]

6-(3-Aminopyrrolidin-1-yl)[1,2,4]triazolo[1,5-a]pyridin-2-amine (2.47 g, 7.77 mmol) from example Int04.05 was suspended in dry THF (40 mL) and cooled to <5° C. 1-Fluoro-4-(isocyanatomethyl)benzene (1.29 g, 8.55 mmol) was added. After 10 min, the mixture was warmed to rt and stirring was continued for 2 h. The mixture was diluted with ethyl acetate and washed with satd. ammonium chloride solution. The organic layer was dried over sodium sulphate, and the solvent was removed in vacuo. The crude product was purified by preparative HPLC to yield the title compound.

$^1$H-NMR (400 MHz, DMSO-d$_6$): δ [ppm]=1.83 (d, 1H), 2.19 (d, 1H), 3.01 (dd, 1H), 3.16-3.26 (m, 1H), 3.28-3.36 (m, 1H), 3.43 (dd, 1H), 4.19 (d, 2H), 4.29 (d, 1H), 5.70 (br. s., 2H), 6.29 (t, 1H), 6.33 (d, 1H), 7.08 (dd, 1H), 7.13 (t, 2H), 7.24 (d, 1H), 7.28 (dd, 2H), 7.73 (d, 1H).

Intermediate Example Int05.01

N-ethyl-3-hydroxy-4-iodobenzamide

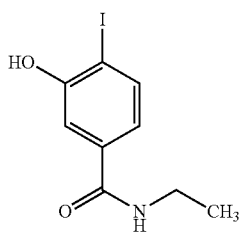

3-Hydroxy-4-iodobenzoic acid (WO2006/18325) (3.00 g, 11.4 mmol) was dissolved in THF (50 mL) and ethylamine (2M solution in THF, 6.8 mL, 13.6 mmol), N-ethyl-diisopropylamine (1.76 g, 13.6 mmol), and HATU (5.18 g, 13.6 mmol) were added. The mixture was stirred overnight at rt. Subsequently, it was diluted with ethyl acetate (200 mL) and washed with ½ satd. aqueous ammonium chloride solution, satd. aqueous sodium bicarbonate solution, and brine. The organic layer was dried over sodium sulphate, and the solvent was evaporated. The residue was triturated with DCM, and the precipitate was collected by suction filtration to yield 1.67 g (49% yield) of the title compound.

¹H-NMR (400 MHz, DMSO-d₆): δ [ppm]=1.10 (t, 3H), 3.20-3.28 (m, 2H), 7.04 (dd, 1H), 7.32 (d, 1H), 7.74 (d, 1H), 8.42 (t, 1H), 10.52 (br. s, 1H).

Intermediate Example Int05.02

3-ethoxy-N-ethyl-4-iodobenzamide

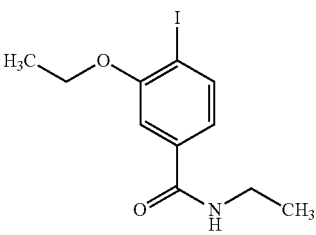

A mixture of N-ethyl-3-hydroxy-4-iodobenzamide (1.00 g, 3.44 mmol) from example Int05.01, iodoethane (563 mg (3.61 mmol), potassium carbonate (950 mg, 6.88 mmol) and acetonitrile (0.29 mL) in DMF (7.3 mL) was heated in a microwave oven for 30 min to 150° C. The reaction mixture was diluted with water and extracted three times with ethyl acetate. The combined organic layers were washed three times with satd. ammonium chloride solution and then with satd. sodium bicarbonate solution and brine, dried over sodium sulphate and evaporated to yield 967 mg (88%) of the title compound.

¹H-NMR (400 MHz, DMSO-d₆): δ [ppm]=1.12 (t, 3H), 1.39 (t, 3H), 3.28 (qd, 2H), 4.14 (q, 2H), 7.21 (dd, 1H), 7.37 (d, 1H), 7.85 (d, 1H), 8.52 (t, 1H).

Intermediate Example Int06.01

N-tert-butyl-3-hydroxy-4-iodobenzamide

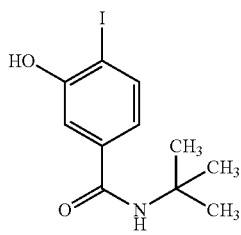

3-Hydroxy-4-iodobenzoic acid (WO2006/18325) (3.00 g, 11.4 mmol) was dissolved in THF (50 mL) and tert-butylamine (997 mg, 13.6 mmol), N-ethyl-diisopropylamine (1.76 g, 13.6 mmol), and HATU (5.18 g, 13.6 mmol) were added. The mixture was stirred overnight at rt. Subsequently, it was diluted with ethyl acetate (400 mL) and washed with satd. aqueous sodium bicarbonate solution, ammonium chloride solution, buffer solution (pH 2), and brine. The organic layer was dried over sodium sulphate, and the solvent was evaporated. The residue was purified by column chromatography on silica gel (eluent:cyclohexane/ethyl acetate gradient 4:1 to 1:1) to yield 2.5 g (60% yield, 88% purity) of the title compound.

¹H-NMR (400 MHz, DMSO-d₆): δ [ppm]=1.35 (s, 9H), 7.00 (dd, 1H), 7.24 (d, 1H), 7.68-7.72 (m, 2H), 10.49 (br. s, 1H).

Intermediate Example Int06.02

N-tert-butyl-4-iodo-3-(2,2,2-trifluoroethoxy)benzamide

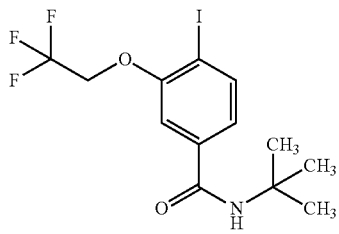 [SMILES: CC(C)(C)NC(=O)c1ccc(I)c(OCC(F)(F)F)c1]

N-tert-butyl-3-hydroxy-4-iodobenzamide (Int06.01) (1.20 g, 3.76 mmol) was dissolved in DMF (7.8 mL) and acetonitrile (0.3 mL), and potassium carbonate (1.04 g, 7.52 mmol) and 2,2,2-trifluoroethyl trifluoromethanesulfonate (916 mg, 3.95 mmol) were added. The mixture was heated in a microwave oven for 30 min to 150° C. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulphate, and the solvent was evaporated to yield 1.43 g (93%) of the title compound as white crystals.

¹H-NMR (400 MHz, DMSO-d₆): δ [ppm]=1.38 (s, 9H), 4.91 (q, 2H), 7.28 (dd, 1H), 7.45 (d, 1H), 7.78 (br. s, 1H), 7.87 (d, 1H).

Intermediate Example Int07.01

N,N-diethyl-3-hydroxy-4-iodobenzamide

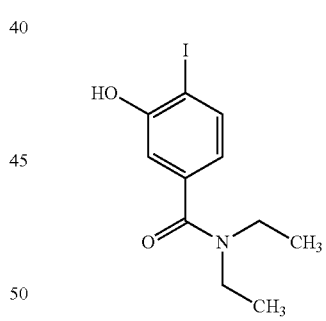

3-Hydroxy-4-iodobenzoic acid (WO2006/18325) (10.0 g, 37.9 mmol) was dissolved in a mixture of DCM (75 mL) and DMF (50 mL) and cooled to 0° C. Oxalyl chloride (7.21 g, 56.8 mmol) was added, and the mixture was stirred for 10 min. Subsequently, diethylamine (6.93 g, 94.7 mmol) was added, and the mixture was warmed to r.t. and stirred for 1.5 h. The reaction mixture was then diluted with water and three times extracted with ethyl acetate. The combined organic layers were washed with aqueous buffer solution (pH 2), satd. sodium bicarbonate solution, and brine, then dried over sodium sulphate, and the solvent was evaporated. The title compound (8.40 g, 66%) was obtained as an oil.

¹H-NMR (400 MHz, DMSO-d₆): δ [ppm]=1.07 (br. s, 6H), 3.16 (br. s, 2H), 3.39 (br. s, 2H), 6.55 (dd, 1H), 6.80 (d, 1H), 7.71 (d, 1H), 10.56 (br. s, 1H).

Intermediate Example Int07.02

N,N-diethyl-4-iodo-3-propoxybenzamide

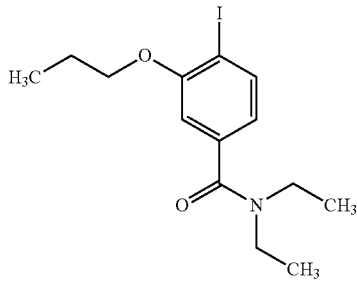 [SMILES: CCCOc1cc(C(=O)N(CC)CC)ccc1I]

N,N-diethyl-3-hydroxy-4-iodobenzamide (Int07.01) (630 mg, 1.97 mmol) was dissolved in DMF (4.2 mL) and acetonitrile (0.17 mL), and potassium carbonate (546 mg, 3.95 mmol) and 1-iodopropane (352 mg, 2.07 mmol) were added. The mixture was heated for 30 min in a microwave oven to 150° C. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulphate, and the solvent was evaporated to yield 670 mg (94%) of the title compound as an oil.

$^1$H-NMR (400 MHz, DMSO-$d_6$): δ [ppm]=1.00-1.18 (m, 6H), 1.03 (t, 3H), 1.69-1.80 (m, 2H), 3.10-3.25 (m, 2H), 3.35-3.47 (m, 2H), 4.02 (t, 2H), 6.69 (dd, 1H), 6.90 (d, 1H), 7.80 (d, 1H).

Intermediate Example Int07.03

N,N-diethyl-4-iodo-3-(2-methylpropoxy)benzamide

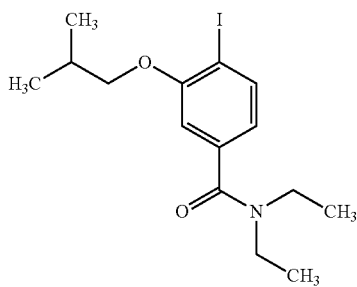 [SMILES: CCN(CC)C(=O)c1ccc(I)c(OCC(C)C)c1]

N,N-diethyl-3-hydroxy-4-iodobenzamide (424 mg, 1.33 mmol) from example Int07.01, 1-iodo-2-methylpropane (257 mg, 1.40 mmol) and potassium carbonate (367 mg, 2.66 mmol) were heated in a mixture of acetonitrile (0.11 mL) and DMF (2.7 mL) in a microwave oven for 30 min to 150° C. Then further 1-iodo-2-methylpropane (257 mg, 1.40 mmol) was added, and the mixture was heated for another 30 min. The reaction mixture was then diluted with water and extracted three times with ethyl acetate. The combined organic layers were washed with satd. ammonium chloride solution, satd. sodium bicarbonate solution and brine. It was then dried over sodium sulphate, and the solvent was evaporated to yield 320 mg (59%) of the title compound.

$^1$H-NMR (400 MHz, DMSO-$d_6$): δ [ppm]=1.03 (d, 6H), 1.04-1.20 (m, 6H), 1.96-2.11 (m, 1H), 3.17 (br. s., 2H), 3.41 (br. s., 2H), 3.84 (d, 2H), 6.69 (dd, 1H), 6.89 (d, 1H), 7.80 (d, 1H).

Intermediate Example Int07.04

3-(cyclopropylmethoxy)-N,N-diethyl-4-iodobenzamide

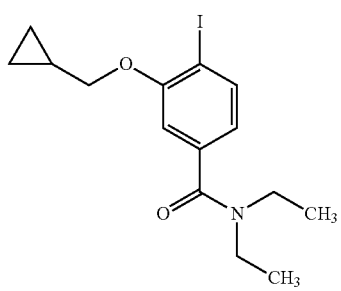 [SMILES: CCN(CC)C(=O)c1ccc(I)c(OCC2CC2)c1]

N,N-diethyl-3-hydroxy-4-iodobenzamide Int07.01 (618 mg, 1.94 mmol) was dissolved in DMF (2.7 mL) and acetonitrile (0.1 mL), and potassium carbonate (535 mg, 3.87 mmol) and 1-(bromomethyl)cyclopropane (275 g, 2.03 mmol) were added. The mixture was heated for 30 min in a microwave oven to 150° C. Subsequently, the reaction mixture was diluted with water and extracted three times with ethyl acetate. The combined organic layers were washed three times with aqueous ammonium chloride solution, then with satd. aqueous sodium bicarbonate solution and with brine. It was dried over sodium sulphate, and the solvent was evaporated to yield 498 mg (63%) of the title compound as an oil.

$^1$H-NMR (400 MHz, DMSO-$d_6$): δ [ppm]=0.34-0.40 (m, 2H), 0.54-0.60 (m, 2H), 0.99-1.08 (m, 3H), 1.09-1.16 (m, 3H), 1.17-1.28 (m, 1H), 3.09-3.23 (m, 2H), 3.35-3.45 (m, 2H), 3.94 (d, 2H), 6.68 (dd, 1H), 6.89 (d, 1H), 7.80 (d, 1H).

Intermediate Example Int07.05

N,N-diethyl-4-iodo-3-(2-methoxyethoxy)benzamide

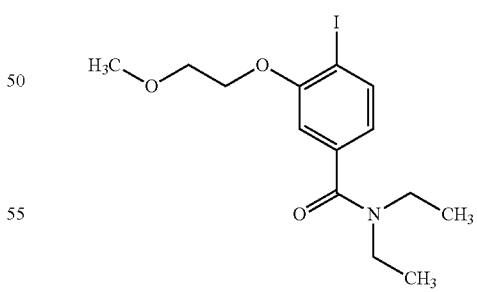

N,N-Diethyl-3-hydroxy-4-iodobenzamide Int07.01 (423 mg, 1.33 mmol) was dissolved in DMF (2.8 mL) and acetonitrile (0.11 mL), and potassium carbonate (366 mg, 2.65 mmol) and 1-bromo-2-methoxyethane (193 mg, 1.39 mmol) were added. The mixture was heated for 30 min in a microwave oven to 150° C. Thereafter, further 1-bromo-2-methoxyethane (193 mg, 1.39 mmol) was added, and the mixture was heated for additional 30 min. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulphate, and the solvent was evaporated to yield 470 mg (94%) of the title compound as an oil.

$^1$H-NMR (400 MHz, DMSO-d$_6$): δ [ppm]=0.98-1.19 (m, 6H), 3.10-3.24 (m, 2H), 3.35 (s, 3H), 3.36-3.47 (m, 2H), 3.68-3.71 (m, 2H), 4.17-4.20 (m, 2H), 6.70 (dd, 1H), 6.94 (d, 1H), 7.81 (d, 1H).

Intermediate Example Int07.06

N,N-diethyl-4-iodo-3-(2,2,2-trifluoroethoxy)benzamide

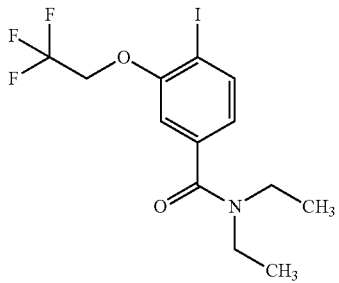 [SMILES: CCN(CC)C(=O)c1ccc(I)c(OCC(F)(F)F)c1]

N,N-diethyl-3-hydroxy-4-iodobenzamide Int07.01 (1.00 g, 3.13 mmol) was dissolved in DMF (6.5 mL) and acetonitrile (0.26 mL), and potassium carbonate (866 mg, 6.27 mmol) and 2,2,2-trifluoroethyl trifluoromethanesulfonate (764 mg, 3.29 mmol) were added. The mixture was heated for 30 min in a microwave oven to 150° C. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulphate, and the solvent was evaporated to yield 1.25 g (99%) of the title compound as an oil.

$^1$H-NMR (400 MHz, DMSO-d$_6$): δ [ppm]=0.99-1.18 (m, 6H), 3.11-3.22 (m, 2H), 3.36-3.47 (m, 2H), 4.89 (q, 2H), 6.79 (dd, 1H), 7.11 (d, 1H), 7.86 (d, 1H).

Intermediate Example Int08.01

(3-hydroxy-4-iodophenyl)(morpholin-4-yl)methanone

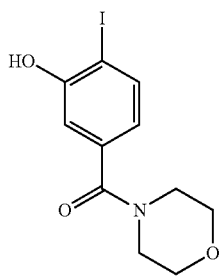

3-Hydroxy-4-iodobenzoic acid (WO2006/18325) (15.0 g, 56.8 mmol) was dissolved in a mixture of DCM (131 mL) and DMF (92 mL) and cooled to 0° C. Oxalyl chloride (10.8 g, 85.2 mmol) was added, and the mixture was stirred for 10 min. Subsequently, morpholine (34.6 g, 398 mmol) was added, and the mixture was warmed to r.t. The reaction mixture was then diluted with ethyl acetate and water. The aqueous phase was acidified to pH 2 with 4N aqueous hydrochloric acid, and the organic layer was separated. It was washed twice with water (pH 2), aqueous sodium bicarbonate solution (pH 8), brine, and conc. ammonium chloride solution. The organic layer was dried over sodium sulphate, and the solvent was evaporated. The residue was triturated with tert-butyl methyl ether and collected by suction filtration to yield 14.8 g (78%) of the title compound.

$^1$H-NMR (400 MHz, DMSO-d$_6$): δ [ppm]=3.57 (br. s., 8H), 6.61 (dd, 1H), 6.86 (d, 1H), 7.73 (d, 1H), 10.61 (br. s, 1H).

Intermediate Example Int08.02

(3-ethoxy-4-iodophenyl)(morpholin-4-yl)methanone

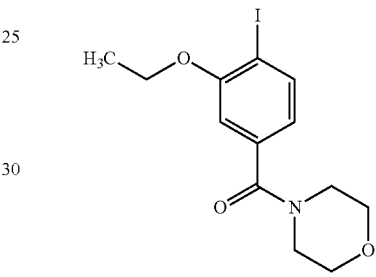

A mixture of (3-hydroxy-4-iodophenyl)(morpholin-4-yl)methanone (1.00 g, 3.00 mmol) from example Int08.01, iodoethane (492 mg (3.15 mmol), potassium carbonate (830 mg, 6.00 mmol) and acetonitrile (0.26 mL) in DMF (6.4 mL) was heated in a microwave oven for 30 min to 150° C. The reaction mixture was diluted with water and extracted three times with ethyl acetate. The combined organic layers were washed three times with satd. ammonium chloride solution and then with satd. sodium bicarbonate solution and brine, dried over sodium sulphate and evaporated to yield 1.05 g (97%) of the title compound.

$^1$H-NMR (400 MHz, DMSO-d$_6$): δ [ppm]=1.36 (t, 3H), 3.47-3.70 (m, 8H), 4.12 (q, 2H), 6.75 (dd, 1H), 6.97 (d, 1H), 7.82 (d, 1H).

Intermediate Example Int08.03

[4-iodo-3-(2,2,2-trifluoroethoxy)phenyl](morpholin-4-yl)methanone

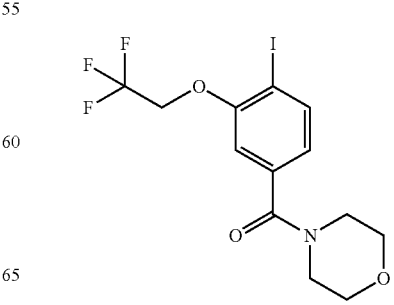

(3-Hydroxy-4-iodophenyl)(morpholin-4-yl)methanone, Int08.01, (2.00 g, 6.00 mmol) was dissolved in DMF (12.4 mL) and acetonitrile (0.5 mL) and potassium carbonate (1.66 g, 1.66 mmol) and 2,2,2-trifluoroethyl trifluoromethanesulfonate (1.46 g, 6.30 mmol) were added. The mixture was heated for 30 min in a microwave oven to 150° C. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulphate, and the solvent was evaporated to yield 2.47 g (99%) of the title compound as an oil.

$^1$H-NMR (400 MHz, DMSO-d$_6$): δ [ppm]=3.47-3.71 (m, 8H), 4.89 (q, 2H), 6.86 (dd, 1H), 7.15 (d, 1H), 7.88 (d, 1H).

Intermediate Example Int09.01

1-(4-bromo-3-methoxyphenyl)piperazine

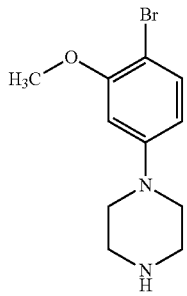

1-(3-Methoxyphenyl)piperazine dihydrochloride (11.97 g, 45.1 mmol) and sodium acetate (4.07 g, 49.7 mmol) were added to a mixture of water (77 ml) and glacial acetic acid (360 ml) at 5° C. Bromine (7.93 g, 49.7 mmol) was added slowly and the mixture was stirred at 0° C. for 1 h. Subsequently, the solvents were removed in vacuo. This residue was dissolved in ethyl acetate and washed with 1N sodium hydroxide solution. The organic layer was dried (sodium sulphate) and the solvent was evaporated. HPLC separation gave 4.39 g of the title compound.

1H-NMR (400 MHz, DMSO-d$_6$): δ [ppm]=2.79-2.83 (m, 4H), 3.03-3.08 (m, 4H), 3.33 (br. s., 1H), 3.81 (s, 3H), 6.42 (dd, 1H), 6.59 (d, 1H), 7.30 (d, 1H).

Intermediate Example Int09.02

1-(4-bromo-3-methoxyphenyl)-4-methylpiperazine

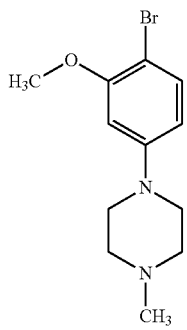 [SMILES: COc1cc(N2CCN(C)CC2)ccc1Br]

To a stirred solution of Int09.01 (1.0 g, 3.69 mmol) in methanol (60 mL) were added acetic acid (0.42 ml) and after 5 min sodium cyanoborohydride (463 mg, 7.38 mmol). After additional 5 min formaldehyde solution (33% in water; 0.59 ml, 7.38 mmol) was added. The reaction mixture was stirred at 60° C. for 16 h. Subsequently, the solvents were removed in vacuo. This residue was dissolved in ethyl acetate and washed with 1N sodium hydroxide solution. The organic layer was dried (sodium sulphate) and the solvent was evaporated. Crystallizaion from pentanes/tert-butyl methyl ether gave 961 mg (91%) of the title compound.

$^1$H-NMR (400 MHz, DMSO-d$_6$): δ [ppm]=2.21 (s, 3H), 2.41-2.46 (m, 4H), 3.12-3.17 (m, 4H), 3.81 (s, 3H), 6.44 (dd, 1H), 6.61 (d, 1H), 7.30 (d, 1H).

Intermediate Example Int10.01

(4-bromo-2-methoxyphenyl)(morpholin-4-yl)methanone

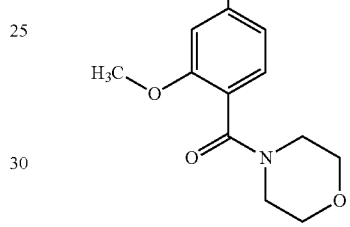

4-Bromo-2-methoxybenzoic acid (WO2010/71741) (2.00 g, 8.66 mmol) in DCM (20 mL) and DMF (14 mL) was cooled to 0° C. and treated with ethanedioyl dichloride (1.65 g, 13.0 mmol) and stirred for 10 min. Subsequently, morpholine (1.89 g, 21.6 mmol) was added, and the mixture was warmed to rt. After consumption of the starting material, water was added, and the mixture was extracted three times with ethyl acetate. The combined organic layers were washed with buffer solution (pH 2), satd. sodium bicarbonate solution and brine, and was dried over sodium sulphate. The solvent was evaporated to yield 2.30 g (89%) of the title compound.

$^1$H-NMR (400 MHz, DMSO-d$_6$): δ [ppm]=3.08-3.13 (m, 2H), 3.49 (t, 2H), 3.56-3.65 (m, 4H), 3.83 (s, 3H), 7.16 (d, 1H), 7.20 (dd, 1H), 7.30 (d, 1H).

Intermediate Example Int11.01

3-bromo-2-ethoxypyridine

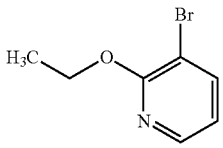

3-Bromo-2-chloropyridine (10.0 g, 52.0 mmol) was dissolved in ethanol (100 mL) and a solution of sodium ethylate in ethanol (70.8 mL, 21%) was added. The mixture was heated to reflux overnight. The solvent was then removed in vacuo and the residue was dissolved in ethyl acetate and washed with satd. aqueous ammonium chloride solution. The organic layer was dried over sodium sulphate, and the solvent was evaporated. The crude product was purified by column chromatography on silica gel (eluent: cyclohexane/ethyl acetate 10:1) to yield 7.26 g (69%) of an yellow oil.

$^1$H-NMR (400 MHz, DMSO-$d_6$): δ [ppm]=1.34 (t, 3H), 4.37 (q, 2H), 6.93 (dd, 1H), 8.02 (dd, 1H), 8.15 (dd, 1H).

Intermediate Example Int11.02

3-bromo-2-(2, 2, 2-trifluoroethoxy)pyridine

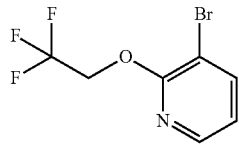 [SMILES: FC(F)(F)COc1ncccc1Br]

2,2,2-Trifluoroethanol (7.80 g, 77.9 mmol) was dissolved in THF (200 mL) and sodium hydride (3.12 g, 77.9 mmol, 60% in mineral oil) was added. The mixture was stirred for 30 min at rt. The solution was subsequently cooled to <5° C. and 3-bromo-2-chloropyridine (3.00 g, 15.6 mmol) was added as a solution in THF (10 mL). The mixture was heated for 48 h to 50° C. Satd. aqueous ammonium chloride solution was added, and the solvent was removed in vacuo. The residue was diluted in ethyl acetate and washed with water. The organic layer was dried over sodium sulphate, and the solvent was evaporated. The crude product was purified by column chromatography on silica gel (eluent: cyclohexane/ethyl acetate 20:1) to yield 2.55 g (64% yield) of the title compound as an oil.

$^1$H-NMR (400 MHz, DMSO-$d_6$): δ [ppm]=5.07 (q, 2H), 7.09 (dd, 1H), 8.15 (dd, 1H), 8.21 (dd, 1H).

Compounds of the Present Invention

Example01.01

4-(2-{[2-ethoxy-4-(ethylcarbamoyl)phenyl]amino}[1,2,4]triazolo[1,5-a]-pyridin-6-yl)-N-(4-fluorobenzyl)piperazine-1-carboxamide

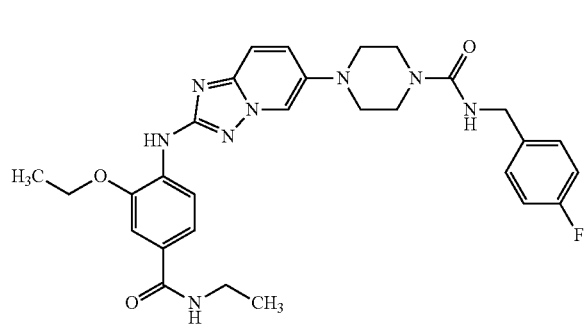 [SMILES: CCNC(=O)c1ccc(Nc2nc3ccc(N4CCN(C(=O)NCc5ccc(F)cc5)CC4)cn3n2)c(OCC)c1]

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and 3-ethoxy-N-ethyl-4-iodobenzamide (109 mg, 0.33 mmol) from example Int05.02 were reacted to give 100 mg (65%) of the title compound.

$^1$H-NMR (400 MHz, DMSO-$d_6$): δ [ppm]=1.13 (t, 3H), 1.45 (t, 3H), 3.06-3.11 (m, 4H), 3.28 (q, 2H), 3.48-3.54 (m, 4H), 4.19 (q, 2H), 4.24 (d, 2H), 7.09-7.17 (m, 2H), 7.25 (t, 1H), 7.28-7.33 (m, 2H), 7.46-7.54 (m, 3H), 7.62 (dd, 1H), 7.95 (s, 1H), 8.28-8.33 (m, 3H).

Example01.02

4-(2-{[4-(tert-butylcarbamoyl)-2-(2,2,2-trifluoroethoxy)phenyl]amino}-[1,2,4]triazolo[1,5-a]pyridin-6-yl)-N-(4-fluorobenzyl)piperazine-1-carboxamide

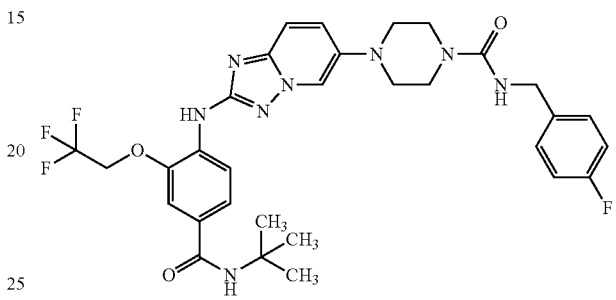

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and N-tert-butyl-4-iodo-3-(2,2,2-trifluoroethoxy)benzamide (130 mg, 0.33 mmol) from example Int06.02 were reacted to give 93 mg (52%) of the title compound.

$^1$H-NMR (400 MHz, DMSO-$d_6$): δ [ppm]=1.40 (s, 9H), 3.06-3.11 (m, 4H), 3.50 (d, 4H), 4.24 (d, 2H), 4.94 (q, 2H), 7.10-7.16 (m, 2H), 7.24 (t, 1H), 7.28-7.33 (m, 2H), 7.51-7.60 (m, 4H), 7.63 (dd, 1H), 7.94 (s, 1H), 8.29-8.33 (m, 2H).

Example01.03

4-(2-{[4-(diethylcarbamoyl)-2-methoxyphenyl]amino}[1,2,4]triazolo[1,5-a]pyridin-6-yl)-N-(4-fluorobenzyl)piperazine-1-carboxamide

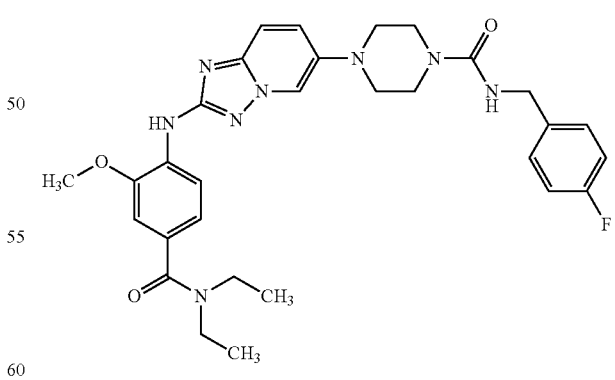

N,N-diethyl-3-methoxy-4-{[6-(piperazin-1-yl)[1,2,4]triazolo[1,5-a]pyridin-2-yl]-amino}benzamide (70 mg, 0.17 mmol) from example Int01.08 was suspended in dry THF (1 mL). 1-Fluoro-4-(isocyanatomethyl)benzene (27 mg, 0.18 mmol) was added, and stirring was continued for 1 h. The mixture was then concentrated in vacuo. The product was isolated after thin layer chromatography on silica gel (eluent DCM/MeOH 20:1) to yield 48 mg (51%) of the title compound.

¹H-NMR (400 MHz, DMSO-d₆): δ [ppm]=1.13 (t, 6H), 3.06-3.10 (m, 4H), 3.31-3.40 (m, 4H), 3.48-3.53 (m, 1H), 3.90 (s, 3H), 4.22-4.26 (m, 2H), 6.96-6.99 (m, 2H), 7.09-7.16 (m, 2H), 7.24 (t, 1H), 7.27-7.33 (m, 2H), 7.50 (d, 1H), 7.60 (dd, 1H), 7.97 (s, 1H), 8.26-8.29 (m, 2H).

Example01.04

4-(2-{[2-ethoxy-4-(morpholin-4-ylcarbonyl)phenyl]amino}[1,2,4]triazolo-[1,5-a]pyridin-6-yl)-N-(4-fluorobenzyl)piperazine-1-carboxamide

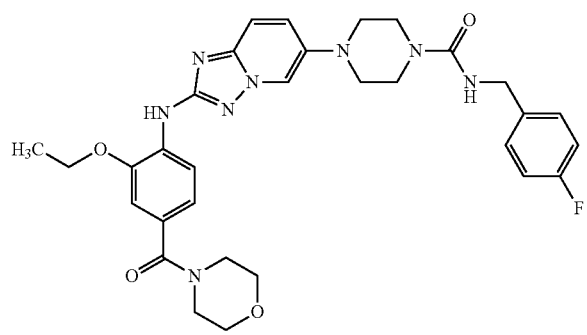 [SMILES: CCOc1cc(C(=O)N2CCOCC2)ccc1Nc1nc2ccc(N3CCN(C(=O)NCc4ccc(F)cc4)CC3)cn2n1]

Following general procedure 1B, 4-(2-amino[1,2,4]triazolo[1,5-a]pyridin-6-yl)-N-(4-fluorobenzyl)piperazine-1-carboxamide (82 mg, 0.22 mmol) from example Int01.06 and (3-ethoxy-4-iodophenyl)(morpholin-4-yl)methanone (120 mg, 0.33 mmol) from example Int08.02 were reacted to give 65 mg (47%) of the title compound.

¹H-NMR (400 MHz, DMSO-d₆): δ [ppm]=1.43 (t, 3H), 3.05-3.10 (m, 4H), 3.48-3.54 (m, 8H), 3.58-3.63 (m, 4H), 4.17 (q, 2H), 4.22-4.26 (m, 2H), 7.02-7.05 (m, 2H), 7.10-7.16 (m, 2H), 7.24 (t, 1H), 7.27-7.33 (m, 2H), 7.51 (d, 1H), 7.61 (dd, 1H), 7.93 (s, 1H), 8.28 (d, 1H), 8.31 (d, 1H).

Example01.05

4-(2-{[4-(diethylcarbamoyl)-2-propoxyphenyl]amino}[1,2,4]triazolo[1,5-a]pyridin-6-yl)-N-(4-fluorobenzyl)piperazine-1-carboxamide

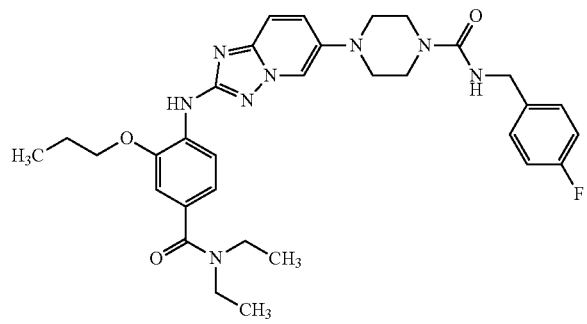 [SMILES: CCCOc1cc(C(=O)N(CC)CC)ccc1Nc1nc2ccc(N3CCN(C(=O)NCc4ccc(F)cc4)CC3)cn2n1]

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and N,N-diethyl-4-iodo-3-propoxybenzamide (117 mg, 0.33 mmol) from example Int07.02 were reacted to give 83 mg (51%) of the title compound.

¹H-NMR (400 MHz, DMSO-d₆): δ [ppm]=1.03 (t, 3H), 1.09-1.16 (m, 6H), 1.83 (sxt, 2H), 3.04-3.11 (m, 4H), 3.31-3.38 (m, 4H), 3.47-3.54 (m, 4H), 4.06 (t, 2H), 4.24 (d, 2H), 6.95-6.99 (m, 2H), 7.13 (t, 2H), 7.24 (t, 1H), 7.30 (dd, 2H), 7.50 (d, 1H), 7.61 (dd, 1H), 7.82 (s, 1H), 8.26-8.31 (m, 2H).

Example01.06

4-(2-{[4-(diethylcarbamoyl)-2-(2-methylpropoxy)phenyl]amino}[1,2,4]-triazolo[1,5-a]pyridin-6-yl)-N-(4-fluorobenzyl)piperazine-1-carboxamide trifluoroacetate

Following general procedure 1A, 4-(2-amino[1,2,4]triazolo[1,5-a]pyridin-6-yl)-N-(4-fluorobenzyl)piperazine-1-carboxamide (82 mg, 0.22 mmol) from example Int01.06 and N,N-diethyl-4-iodo-3-(2-methylpropoxy)benzamide (100 mg, 0.27 mmol) from example Int07.03 were reacted to give 7 mg (4%) of the title compound.

¹H-NMR (400 MHz, DMSO-d₆): δ [ppm]=1.03 (d, 6H), 1.12 (t, 6H), 2.14 (spt, 1H), 3.05-3.11 (m, 4H), 3.47-3.53 (m, 4H), 3.60-3.74 (m, 5H), 3.89 (d, 2H), 4.22-4.26 (m, 2H), 6.95-6.99 (m, 2H), 7.09-7.16 (m, 2H), 7.24 (t, 1H), 7.27-7.33 (m, 2H), 7.51 (d, 1H), 7.62 (dd, 1H), 7.80 (s, 1H), 8.26 (d, 1H), 8.31 (d, 1H).

Example01.07

4-(2-{[2-(cyclopropylmethoxy)-4-(diethylcarbamoyl)phenyl]amino}[1,2,4]-triazolo[1,5-a]pyridin-6-yl)-N-(4-fluorobenzyl)piperazine-1-carboxamide

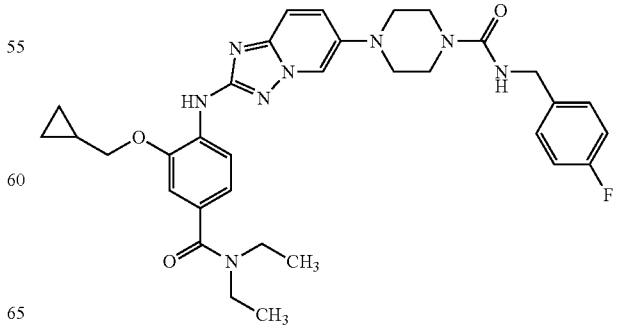

Following general procedure 1A, 4-(2-amino[1,2,4]triazolo[1,5-a]pyridin-6-yl)-N-(4-fluorobenzyl)piperazine-1-carboxamide (82 mg, 0.22 mmol) from example Int01.06 and 3-(cyclopropylmethoxy)-N,N-diethyl-4-iodobenzamide (100 mg, 0.27 mmol) from example Int07.04 were reacted to give 40 mg (29%) of the title compound.

$^{1}$H-NMR (400 MHz, DMSO-d$_{6}$): δ [ppm]=0.35-0.42 (m, 2H), 0.58-0.64 (m, 2H), 1.12 (t, 6H), 1.29-1.39 (m, 1H), 3.05-3.12 (m, 4H), 3.30-3.40 (m, 4H), 3.46-3.55 (m, 4H), 3.96 (d, 2H), 4.24 (d, 2H), 6.94-6.99 (m, 2H), 7.13 (t, 2H), 7.24 (t, 1H), 7.28-7.33 (m, 2H), 7.51 (d, 1H), 7.62 (dd, 1H), 7.77 (s, 1H), 8.26-8.32 (m, 2H).

Example01.08

4-(2-{[4-(diethylcarbamoyl)-2-(2-methoxyethoxy)phenyl]amino}[1,2,4]-triazolo[1,5-a]pyridin-6-yl)-N-(4-fluorobenzyl)piperazine-1-carboxamide

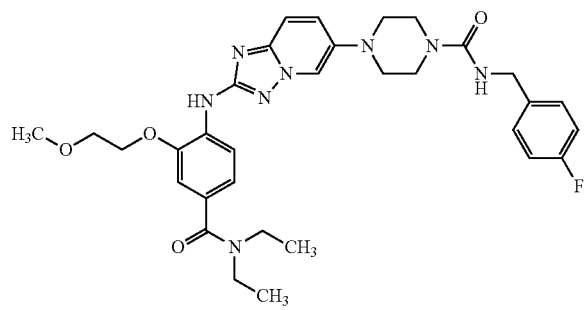 [SMILES: CCN(CC)C(=O)c1ccc(Nc2nc3ccc(N4CCN(C(=O)NCc5ccc(F)cc5)CC4)cn3n2)c(OCCOC)c1]

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and N,N-diethyl-4-iodo-3-(2-methoxyethoxy)benzamide (123 mg, 0.33 mmol) from example Int07.05 were reacted to give 57 mg (34%) of the title compound.

$^{1}$H-NMR (400 MHz, DMSO-d$_{6}$): δ [ppm]=1.08-1.15 (m, 9H), 3.05-3.11 (m, 4H), 3.34-3.39 (m, 4H), 3.47-3.54 (m, 4H), 3.73-3.77 (m, 2H), 4.20-4.26 (m, 4H), 7.00 (d, 1H), 7.03 (s, 1H), 7.13 (t, 2H), 7.24 (t, 1H), 7.27-7.33 (m, 2H), 7.51 (d, 1H), 7.58-7.64 (m, 1H), 7.91 (s, 1H), 8.28-8.33 (m, 2H).

Example01.09

4-(2-{[4-(diethylcarbamoyl)-2-(2,2,2-trifluoroethoxy)phenyl]amino}[1,2,4]-triazolo[1,5-a]pyridin-6-yl)-N-(4-fluorobenzyl)piperazine-1-carboxamide trifluoroacetate

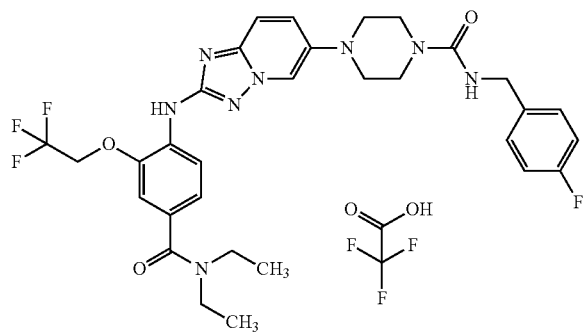 [SMILES: CCN(CC)C(=O)c1ccc(Nc2nc3ccc(N4CCN(C(=O)NCc5ccc(F)cc5)CC4)cn3n2)c(OCC(F)(F)F)c1 ; O=C(O)C(F)(F)F]

Following general procedure 1A, 4-(2-amino[1,2,4]triazolo[1,5-a]pyridin-6-yl)-N-(4-fluorobenzyl)piperazine-1-carboxamide (73 mg, 0.20 mmol) from example Int01.06 and N,N-diethyl-4-iodo-3-(2,2,2-trifluoroethoxy)benzamide (100 mg, 0.24 mmol) from example Int07.06 were reacted to give 14 mg (9%) of the title compound.

$^{1}$H-NMR (400 MHz, DMSO-d$_{6}$): δ [ppm]=1.07-1.16 (m, 6H), 3.05-3.11 (m, 4H), 3.28-3.37 (m, 4H), 3.47-3.53 (m, 4H), 4.22-4.26 (m, 2H), 4.92 (q, 2H), 7.08 (dd, 1H), 7.10-7.16 (m, 2H), 7.18 (d, 1H), 7.22-7.26 (m, 1H), 7.27-7.33 (m, 2H), 7.52 (d, 1H), 7.63 (dd, 1H), 7.93 (s, 1H), 8.27-8.33 (m, 2H).

Example01.10

N-(4-fluorobenzyl)-4-(2-{[2-methoxy-4-(4-methylpiperazin-1-yl)phenyl]-amino}[1,2,4]triazolo[1,5-a]pyridin-6-yl)piperazine-1-carboxamide

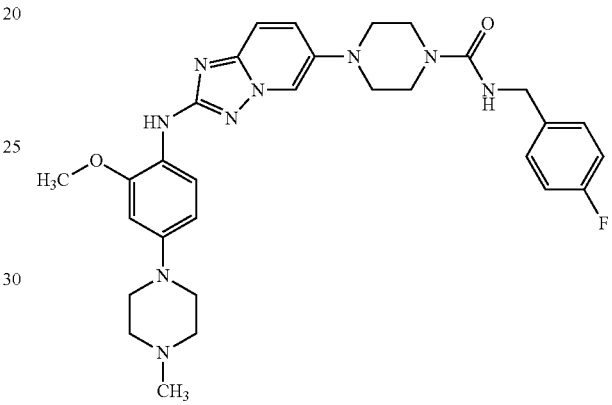

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and 1-(4-bromo-3-methoxyphenyl)-4-methylpiperazine (93 mg, 0.33 mmol) from example Int09.02 were reacted to give 68 mg (42%) of the title compound.

$^{1}$H-NMR (400 MHz, DMSO-d$_{6}$): δ [ppm]=2.25 (s, 3H), 2.46-2.49 (m, 4H), 3.03-3.12 (m, 8H), 3.46-3.52 (m, 4H), 3.84 (s, 3H), 4.24 (d, 2H), 6.49 (dd, 1H), 6.64 (d, 1H), 7.09-7.16 (m, 2H), 7.23 (t, 1H), 7.28-7.32 (m, 2H), 7.41 (d, 1H), 7.47 (s, 1H), 7.53 (dd, 1H), 7.91 (d, 1H), 8.21 (d, 1H).

Example01.11

N-(4-fluorobenzyl)-4-(2-{[3-methoxy-4-(morpholin-4-ylcarbonyl)phenyl]-amino}[1,2,4]triazolo[1,5-a]pyridin-6-yl)piperazine-1-carboxamide

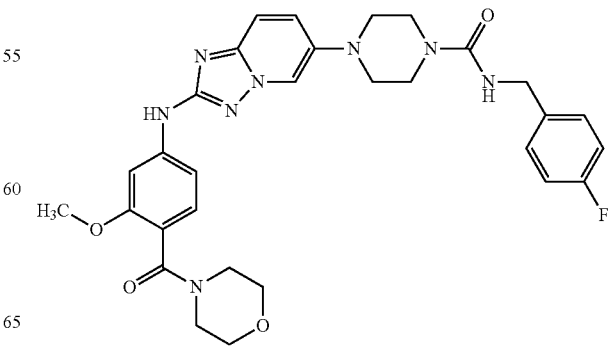

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and (4-bromo-2-methoxyphenyl)(morpholin-4-yl)methanone (98 mg, 0.33 mmol) from example Int10.01 were reacted to give 106 mg (67%) of the title compound.

¹H-NMR (400 MHz, DMSO-d₆): δ [ppm]=3.04-3.11 (m, 4H), 3.11-3.24 (m, 2H), 3.47-3.54 (m, 6H), 3.56-3.63 (m, 4H), 3.81 (s, 3H), 4.24 (d, 2H), 7.08-7.17 (m, 3H), 7.24 (t, 1H), 7.27-7.33 (m, 2H), 7.36 (dd, 1H), 7.43 (d, 1H), 7.49 (d, 1H), 7.58 (dd, 1H), 8.27 (d, 1H), 9.65 (s, 1H).

Example01.12

N-(4-fluorobenzyl)-4-{2-[(2-methoxypyridin-3-yl)amino][1,2,4]triazolo[1,5-a]pyridin-6-yl}piperazine-1-carboxamide

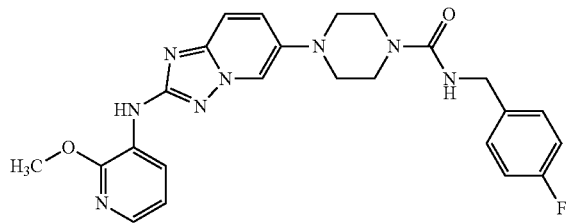 [SMILES: COc1ncccc1Nc1nc2ccc(N3CCN(C(=O)NCc4ccc(F)cc4)CC3)cn2n1]

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and 3-bromo-2-methoxypyridine (61 mg, 0.33 mmol) were reacted to give 86 mg (67%) of the title compound.

¹H-NMR (400 MHz, DMSO-d₆): δ [ppm]=3.05-3.10 (m, 4H), 3.48-3.53 (m, 4H), 3.95 (s, 3H), 4.24 (d, 2H), 6.99 (dd, 1H), 7.09-7.16 (m, 2H), 7.24 (t, 1H), 7.27-7.33 (m, 2H), 7.50 (d, 1H), 7.60 (dd, 1H), 7.70 (dd, 1H), 8.13 (s, 1H), 8.27 (d, 1H), 8.49 (dd, 1H).

Example01.13

4-{2-[(2-ethoxypyridin-3-yl)amino][1,2,4]triazolo[1,5-a]pyridin-6-yl}-N-(4-fluorobenzyl)piperazine-1-carboxamide

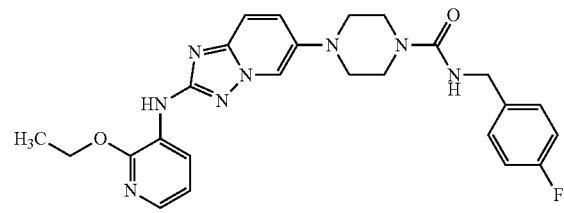 [SMILES: CCOc1ncccc1Nc1nc2ccc(N3CCN(C(=O)NCc4ccc(F)cc4)CC3)cn2n1]

Following general procedure 1A, 4-(2-amino[1,2,4]triazolo[1,5-a]pyridin-6-yl)-N-(4-fluorobenzyl)piperazine-1-carboxamide (100 mg, 0.27 mmol) from example Int01.06 and 3-bromo-2-ethoxypyridine (66 mg, 0.33 mmol) from example Int1.01 were reacted to give 37 mg (28%) of the title compound.

¹H-NMR (400 MHz, DMSO-d₆): δ [ppm]=1.40 (t, 3H), 3.08 (d, 4H), 3.50 (d, 4H), 4.24 (d, 2H), 4.41 (q, 2H), 6.97 (dd, 1H), 7.13 (t, 2H), 7.23 (t, 1H), 7.30 (dd, 2H), 7.50 (d, 1H), 7.60 (dd, 1H), 7.68 (dd, 1H), 7.99 (s, 1H), 8.27 (d, 1H), 8.49 (dd, 1H).

Example01.14

4-{2-[(2-cyanophenyl)amino][1,2,4]triazolo[1,5-a]pyridin-6-yl}-N-(4-fluoro-benzyl)piperazine-1-carboxamide

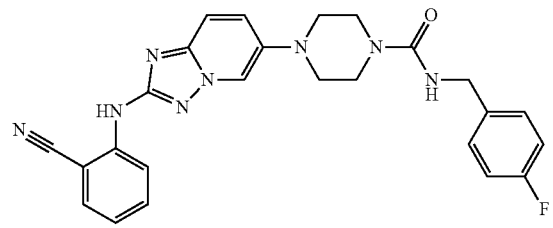 [SMILES: N#Cc1ccccc1Nc1nc2ccc(N3CCN(C(=O)NCc4ccc(F)cc4)CC3)cn2n1]

Following general procedure 1A, 4-(2-amino[1,2,4]triazolo[1,5-a]pyridin-6-yl)-N-(4-fluorobenzyl)piperazine-1-carboxamide (133 mg, 0.36 mmol) from example Int01.06 and 2-bromobenzonitrile (79 mg, 0.43 mmol) were reacted to give 67 mg (40%) of the title compound.

¹H-NMR (400 MHz, DMSO-d₆): δ [ppm]=3.04-3.11 (m, 4H), 3.47-3.53 (m, 4H), 4.24 (d, 2H), 7.09-7.16 (m, 3H), 7.24 (t, 1H), 7.27-7.33 (m, 2H), 7.50 (d, 1H), 7.58-7.66 (m, 2H), 7.72 (dd, 1H), 8.00-8.03 (m, 1H), 8.26 (d, 1H), 9.25 (s, 1H).

Example02.01

1-(2-{[2-ethoxy-4-(morpholin-4-ylcarbonyl)phenyl]amino}[1,2,4]triazolo-[1,5-a]pyridin-6-yl)-N-(4-fluorobenzyl)piperidine-4-carboxamide

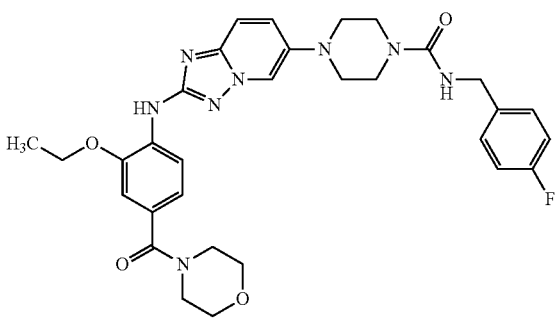 [SMILES: CCOc1cc(C(=O)N2CCOCC2)ccc1Nc1nc2ccc(N3CCN(C(=O)NCc4ccc(F)cc4)CC3)cn2n1]

Following general procedure 1A, 1-(2-amino[1,2,4]triazolo[1,5-a]pyridin-6-yl)-N-(4-fluorobenzyl)piperidine-4-carboxamide (73 mg, 0.18 mmol) from example Int02.05 and (3-ethoxy-4-iodophenyl)(morpholin-4-yl)methanone (79 mg, 0.22 mmol) from example Int08.02 were reacted to give 46 mg (41%) of the title compound.

¹H-NMR (400 MHz, DMSO-d₆): δ [ppm]=1.43 (t, 3H), 1.69-1.88 (m, 4H), 2.29-2.37 (m, 1H), 2.62-2.71 (m, 2H), 3.61 (br. s., 10H), 4.16 (q, 2H), 4.26 (d, 2H), 7.01-7.05 (m, 2H), 7.12-7.18 (m, 2H), 7.25-7.31 (m, 2H), 7.48 (d, 1H), 7.57 (dd, 1H), 7.90 (s, 1H), 8.24 (d, 1H), 8.31 (d, 1H), 8.39 (t, 1H).

Example 03.01

N-(cyclopropylmethyl)-1-(2-{[2-ethoxy-4-(ethylcarbamoyl)phenyl]amino}-[1,2,4]triazolo[1,5-a]pyridin-6-yl)piperidine-4-carboxamide

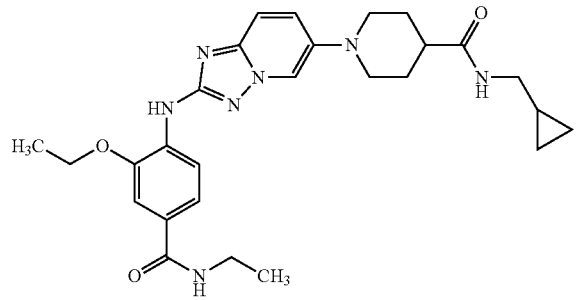 [SMILES: CCNC(=O)c1ccc(Nc2nc3ccc(N4CCC(C(=O)NCC5CC5)CC4)cn3n2)c(OCC)c1]

Following general procedure 1A, 1-(2-amino[1,2,4]triazolo[1,5-a]pyridin-6-yl)-N-(cyclopropylmethyl)piperidine-4-carboxamide (80 mg, 0.25 mmol) from example Int02.06 and 3-ethoxy-N-ethyl-4-iodobenzamide (97 mg, 0.31 mmol) from example Int05.02 were reacted to give 94 mg (73%) of the title compound.

$^1$H-NMR (400 MHz, DMSO-$d_6$): δ [ppm]=0.12-0.17 (m, 2H), 0.39 (dd, 2H), 0.84-0.94 (m, 1H), 1.13 (t, 3H), 1.45 (t, 3H), 1.66-1.83 (m, 4H), 2.22-2.32 (m, 1H), 2.61-2.70 (m, 2H), 2.96 (t, 2H), 3.25-3.32 (m, 2H), 3.59-3.66 (m, 2H), 4.19 (q, 2H), 7.46-7.51 (m, 3H), 7.58 (dd, 1H), 7.90 (t, 1H), 7.93 (s, 1H), 8.26 (d, 1H), 8.28-8.33 (m, 2H).

Example 03.02

N-(cyclopropylmethyl)-1-(2-{[2-ethoxy-4-(morpholin-4-ylcarbonyl)phenyl]-amino}[1,2,4]triazolo[1,5-a]pyridin-6-yl)piperidine-4-carboxamide

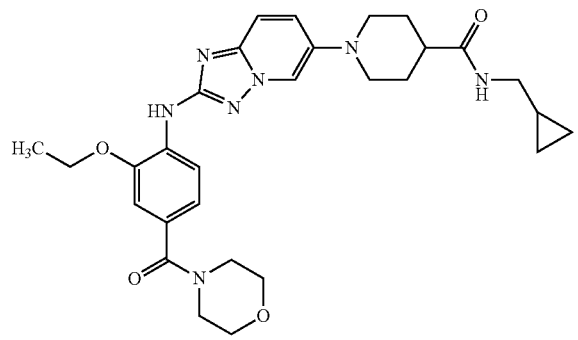 [SMILES: CCOc1cc(C(=O)N2CCOCC2)ccc1Nc1nc2ccc(N3CCC(C(=O)NCC4CC4)CC3)cn2n1]

Following general procedure 1A, 1-(2-amino[1,2,4]triazolo[1,5-a]pyridin-6-yl)-N-(cyclopropylmethyl)piperidine-4-carboxamide (80 mg, 0.25 mmol) from example Int02.06 and (3-ethoxy-4-iodophenyl)(morpholin-4-yl)methanone (110 mg, 0.31 mmol) from example Int08.02 were reacted to give 85 mg (60%) of the title compound.

$^1$H-NMR (400 MHz, DMSO-$d_6$): δ [ppm]=0.12-0.17 (m, 2H), 0.36-0.42 (m, 2H), 0.83-0.94 (m, 1H), 1.43 (t, 3H), 1.66-1.83 (m, 4H), 2.22-2.32 (m, 1H), 2.60-2.70 (m, 2H), 2.96 (t, 2H), 3.47-3.66 (m, 10H), 4.16 (d, 2H), 7.01-7.06 (m, 2H), 7.45-7.50 (m, 1H), 7.57 (dd, 1H), 7.88-7.92 (m, 2H), 8.23 (d, 1H), 8.31 (d, 1H).

Example 03.03

N-(cyclopropylmethyl)-1-(2-{[2-(2,2,2-trifluoroethoxy)pyridin-3-yl]amino}-[1,2,4]triazolo[1,5-a]pyridin-6-yl)piperidine-4-carboxamide

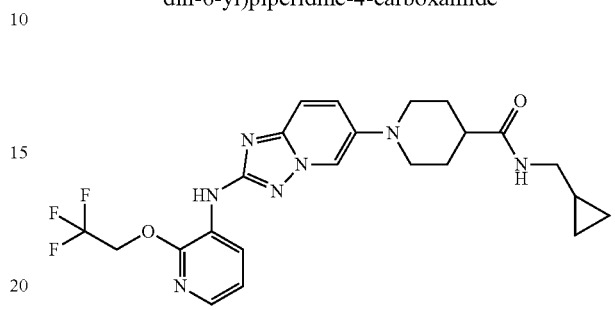

Following general procedure 1A, 1-(2-amino[1,2,4]triazolo[1,5-a]pyridin-6-yl)-N-(cyclopropylmethyl)piperidine-4-carboxamide (80 mg, 0.25 mmol) from example Int02.06 and 3-bromo-2-(2,2,2-trifluoroethoxy)pyridine (78 mg, 0.31 mmol) from example Int11.02 were reacted to give 38 mg (30%) of the title compound.

$^1$H-NMR (400 MHz, DMSO-$d_6$): δ [ppm]=0.12-0.17 (m, 2H), 0.39 (d, 2H), 0.83-0.94 (m, 1H), 1.65-1.82 (m, 4H), 2.22-2.31 (m, 1H), 2.60-2.70 (m, 2H), 2.95 (t, 2H), 3.58-3.65 (m, 2H), 5.07 (q, 2H), 7.12 (dd, 1H), 7.49 (d, 1H), 7.57 (dd, 1H), 7.74 (dd, 1H), 7.90 (t, 1H), 8.20-8.24 (m, 2H), 8.57 (dd, 1H).

Example 04.01

3-ethoxy-N-ethyl-4-{[6-(4-{[(4-fluorophenyl)acetyl]amino}piperidin-1-yl)-[1,2,4]triazolo[1,5-a]pyridin-2-yl]amino}benzamide

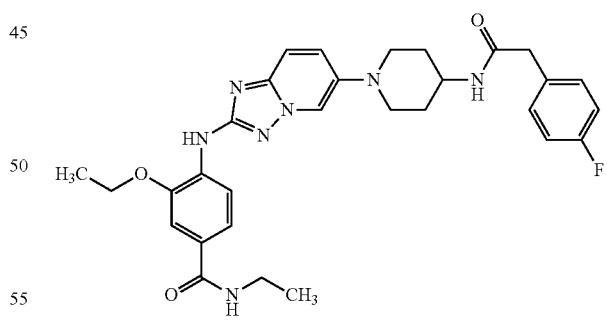

Following general procedure 1B, N-[1-(2-amino[1,2,4]triazolo[1,5-a]pyridin-6-yl)piperidin-4-yl]-2-(4-fluorophenyl)acetamide (100 mg, 0.27 mmol) from example Int03.06 and 3-ethoxy-N-ethyl-4-iodobenzamide (104 mg, 0.33 mmol) from example Int05.02 were reacted to give 58 mg (37%) of the title compound.

$^1$H-NMR (400 MHz, DMSO-$d_6$): δ [ppm]=1.13 (t, 3H), 1.45 (t, 3H), 1.50-1.61 (m, 2H), 1.79-1.90 (m, 2H), 2.74-2.83 (m, 2H), 3.25-3.30 (m, 2H), 3.40 (s, 2H), 3.52-3.59 (m, 2H), 3.64-3.75 (m, 1H), 4.19 (q, 2H), 7.09-7.16 (m, 2H), 7.26-7.32 (m, 2H), 7.47-7.51 (m, 3H), 7.58 (dd, 1H), 7.93 (s, 1H), 8.10 (d, 1H), 8.26 (d, 1H), 8.28-8.32 (m, 2H).

Example 04.02

N-[1-(2-{[2-ethoxy-4-(morpholin-4-ylcarbonyl)phenyl]amino}[1,2,4]-triazolo[1,5-a]pyridin-6-yl)piperidin-4-yl]-2-(4-fluorophenyl)acetamide

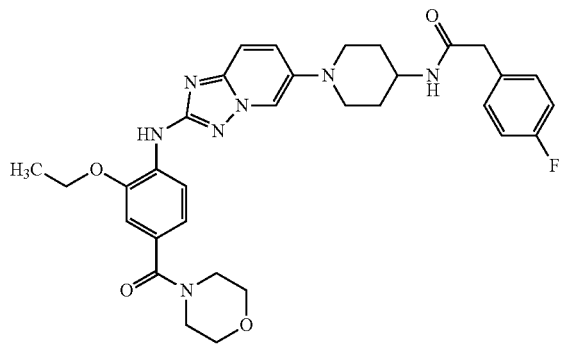 [SMILES: CCOc1cc(C(=O)N2CCOCC2)ccc1Nc1nc2ccc(N3CCC(NC(=O)Cc4ccc(F)cc4)CC3)cn2n1]

Following general procedure 1B, N-[1-(2-amino[1,2,4]triazolo[1,5-a]pyridin-6-yl)piperidin-4-yl]-2-(4-fluorophenyl)acetamide (100 mg, 0.27 mmol) from example Int03.06 and (3-ethoxy-4-iodophenyl)(morpholin-4-yl)methanone (118 mg, 0.33 mmol) from example Int08.02 were reacted to give 58 mg (35%) of the title compound.

$^1$H-NMR (400 MHz, DMSO-d$_6$): δ [ppm]=1.43 (t, 3H), 1.49-1.61 (m, 2H), 1.81-1.89 (m, 2H), 2.73-2.83 (m, 2H), 3.40 (s, 2H), 3.48-3.64 (m, 10H), 3.64-3.75 (m, 1H), 4.16 (q, 2H), 7.01-7.05 (m, 2H), 7.09-7.16 (m, 2H), 7.26-7.31 (m, 2H), 7.47 (d, 1H), 7.57 (dd, 1H), 7.91 (s, 1H), 8.10 (d, 1H), 8.24 (d, 1H), 8.31 (d, 1H).

Example 04.03

N-(1-{2-[(2-ethoxypyridin-3-yl)amino][1,2,4]triazolo[1,5-a]pyridin-6-yl}-piperidin-4-yl)-2-(4-fluorophenyl)acetamide

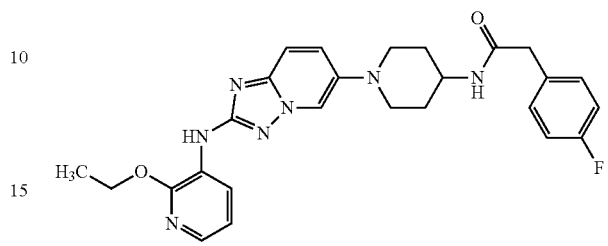

Following general procedure 1B, N-[1-(2-amino[1,2,4]triazolo[1,5-a]pyridin-6-yl)piperidin-4-yl]-2-(4-fluorophenyl)acetamide (100 mg, 0.27 mmol) from example Int03.06 and 3-bromo-2-ethoxypyridine (66 mg, 0.33 mmol) from example Int1 1.01 were reacted to give 72 mg (50%) of the title compound.

$^1$H-NMR (400 MHz, DMSO-d$_6$): δ [ppm]=1.39 (t, 3H), 1.49-1.61 (m, 2H), 1.80-1.88 (m, 2H), 2.73-2.83 (m, 2H), 3.40 (s, 2H), 3.51-3.58 (m, 2H), 3.63-3.74 (m, 1H), 4.40 (q, 2H), 6.97 (dd, 1H), 7.12 (t, 2H), 7.29 (dd, 2H), 7.47 (d, 1H), 7.57 (dd, 1H), 7.68 (dd, 1H), 7.99 (s, 1H), 8.10 (d, 1H), 8.23 (d, 1H), 8.49 (dd, 1H).

Example 05.01

1-(4-fluorobenzyl)-3-[1-(2-{[4-(morpholin-4-ylcarbonyl)-2-(2,2,2-trifluoroethoxy)phenyl]amino}[1,2,4]triazolo[1,5-a]pyridin-6-yl)pyrrolidin-3-yl]urea

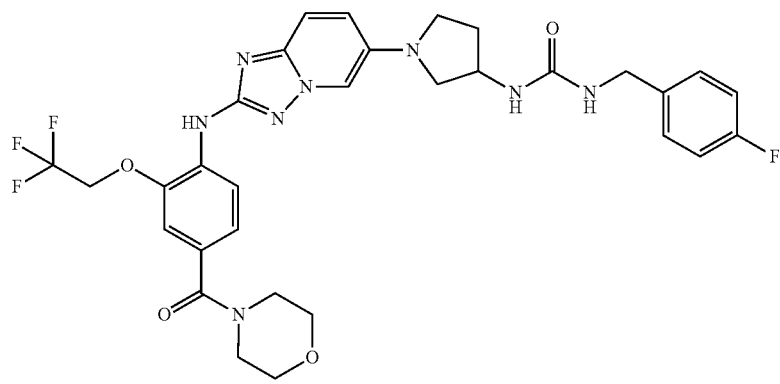 [SMILES: O=C(NCc1ccc(F)cc1)NC1CCN(c2ccc3nc(Nc4ccc(C(=O)N5CCOCC5)cc4OCC(F)(F)F)nn3c2)C1]

Following general procedure 1B, 1-[1-(2-amino[1,2,4]triazolo[1,5-a]pyridin-6-yl)pyrrolidin-3-yl]-3-(4-fluorobenzyl)urea (100 mg, 0.27 mmol) from example Int04.06 and [4-iodo-3-(2,2,2-trifluoroethoxy)phenyl](morpholin-4-yl)methanone (135 mg, 0.33 mmol) from example Int08.03 were reacted to give 41 mg (23%) of the title compound.

¹H-NMR (400 MHz, DMSO-d₆): δ [ppm]=1.82-1.91 (m, 1H), 2.15-2.26 (m, 1H), 3.04-3.10 (m, 1H), 3.23-3.41 (m, 2H), 3.45-3.65 (m, 9H), 4.20 (d, 2H), 4.27-4.35 (m, 1H), 4.92 (q, 2H), 6.29 (t, 1H), 6.35 (d, 1H), 7.10-7.17 (m, 3H), 7.22-7.31 (m, 4H), 7.49 (d, 1H), 7.84 (s, 1H), 7.96 (d, 1H), 8.36 (d, 1H).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Biological Assay: Proliferation Assay

Cultivated tumor cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumor cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µl of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate(=0%) and the extinction of the untreated (0 µm) cells(=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (SEQ ID: 1) (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM MgCl₂, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheinn, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheinn, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC₅₀ values were calculated by a 4 parameter fit using an inhouse software.

The compounds of the present invention are characterized by the following IC₅₀ values, determined in Mps-1 kinase assays (as described above):

| Example No | Mps-1 Inhibition, IC₅₀ (Assay with 10 µM ATP) |
|---|---|
| 01.01 | 3.1 nM |
| 01.02 | 5.6 nM |
| 01.03 | 7.9 nM |
| 01.04 | 2.6 nM |
| 01.05 | 9.7 nM |
| 01.06 | 28.5 nM |
| 01.07 | 20.6 nM |
| 01.08 | 57.0 nM |
| 01.09 | 1.7 nM |

| Example No | Mps-1 Inhibition, IC$_{50}$ (Assay with 10 µM ATP) |
|---|---|
| 01.10 | 9.2 nM |
| 01.11 | 45.6 nM |
| 01.12 | 18.6 nM |
| 01.13 | 8.9 nM |
| 01.14 | 8.0 nM |
| 02.01 | 32.2 nM |
| 03.01 | 68.8 nM |
| 03.02 | 67.8 nM |
| 03.03 | 73.4 nM |
| 04.01 | 7.1 nM |
| 04.02 | 12.8 nM |
| 04.03 | 32.8 nM |
| 05.01 | 46.9 nM |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumor cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2/M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat #16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the IC$_{50}$ value for each tested compound.

Thus the compounds of the present invention effectively inhibit Mps-1 kinase and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haematological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Determination of Metabolic Stability In Vitro
(including calculation of hepatic in vivo blood clearance (CL) and of maximal oral bioavailability ($F_{max}$))

The metabolic stability of test compounds in vitro was determined by incubating them at 1 µM with a suspension liver microsomes in 100 mM phosphate buffer, pH7.4 (NaH$_2$PO$_4$×H$_2$O+Na$_2$HPO$_4$×2H$_2$O) at a protein concentration of 0.5 mg/mL and at 37° C. The reaction was activated by adding a co-factor mix containing 1.2 mg NADP, 3 IU glucose-6-phosphate dehydrogenase, 14.6 mg glucose-6-phosphate and 4.9 mg MgCl$_2$ in phosphate buffer, pH 7.4. Organic solvent in the incubations was limited to <0.2% dimethylsulfoxide (DMSO) and <1% methanol. During incubation, the microsomal suspensions were continuously shaken and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The following parameter values were used: Liver blood flow—1.3 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.

With the described assay only phase-I metabolism of microsomes is reflected, e.g. typically oxidoreductive reactions by cytochrome P450 enzymes and flavin mono-oxygenases (FMO) and hydrolytic reactions by esterases (esters and amides).

The invention claimed is:
1. A compound of formula (I):

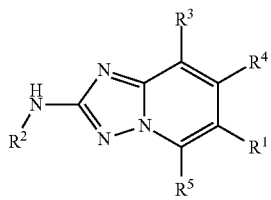

wherein:
$R^1$ is a

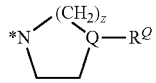

group,
wherein * indicates the point of attachment of said group to the rest of the molecule;
Q is CH or N, with the proviso that Q is CH if $R^Q$ is —N(H)C(=O)$R^6$, —N(H)C(=O)N(H)$R^6$ or —N(H)C(=O)N$R^6R^7$;
$R^Q$ is a group selected from:
—N(H)C(=O)$R^6$, —N(H)C(=O)N(H)$R^6$, —N(H)C(=O)N$R^6R^7$, —C(=O)N(H)$R^6$, and —C(=O)N$R^6R^7$;
$R^2$ is a phenyl- or pyridyl- group which is substituted one or more times, identically or differently, with a substituent selected from $R^{5a}$ and $R^{5b}$;
$R^3$ is a hydrogen atom;
$R^4$ is a hydrogen atom;
$R^5$ is a hydrogen atom;
$R^{5a}$ is a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —N$R^7R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2$ $R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, and —N=S(=O)($R^8$)$R^7$;

$R^{5b}$ is a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —N$R^7R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2$ $R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, and —N=S(=O)($R^8$)$R^7$;

$R^6$ is a group selected from:
—$(CH_2)_q$-aryl, —$(CH_2)_q$-heteroaryl, —$(CH_2)_q$-($C_3$-$C_6$-cycloalkyl), and —$(CH_2)_q$-(3- to 10-membered heterocycloalkyl),
wherein said group is optionally substituted, one or more times, identically or differently, with a substituent selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —NH$_2$, —N(H)$R^8$, —N$R^8R^7$, —C(=O)N(H)$R^8$, —C(=O)

$NR^8R^7$, $R^8$—S—, $R^8$—S(=O)—, $R^8$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, and —N=S(=O)(R$^8$)R$^7$;

$R^7$ is a $C_1$-$C_3$-alkyl- group or a $C_3$-$C_6$-cycloalkyl-group;

$R^8$ is a $C_1$-$C_6$-alkyl- or $C_3$-$C_6$-cycloalkyl-group,
wherein said $C_1$-$C_6$-alkyl- or $C_3$-$C_6$-cycloalkyl- group is optionally substituted, one or more times, identically or differently, with a substituent selected from: halo-, hydroxy-, —NHR$^7$, —NR$^7$R$^7$, —N($C_1$-$C_3$-alkyl)-C(=O)R$^7$, —N($C_1$-$C_3$-alkyl)-C(=O)OR$^7$, $C_1$-$C_3$-alkyl-, R$^7$—S(=O)$_2$—, $C_1$-$C_3$-alkoxy-, and halo-$C_1$-$C_3$-alkoxy-;

or $R^7$ and $R^8$ are taken together with the molecular fragment to which they are attached to form a 4- to 6-membered heterocycloalkyl- group, which is optionally substituted, one or more times, identically or differently, with a halogen atom, a $C_1$-$C_3$-alkyl-, halo-$C_1$-$C_3$-alkyl-or $C_1$-$C_3$-alkoxy-group;

n, m, and p are, independently from each other, an integer of 0, 1, 2 or 3;

q is an integer of 0, 1, 2 or 3; and z is an integer of 1 or 2, or a stereoisomer, a tautomer, an N-oxide, a hydrate, a solvate, or a salt thereof, or a mixture of any of the foregoing.

2. The compound according to claim 1, wherein:
$R^Q$ is a group selected from:
—N(H)C(=O)R$^6$, —N(H)C(=O)N(H)R$^6$, and —C(=O)N(H)R$^6$,
or a tautomer, an N-oxide, a hydrate, a solvate, or a salt thereof, or a mixture of any of the foregoing.

3. The compound according to claim 1, wherein:
$R^1$ is a group selected from:

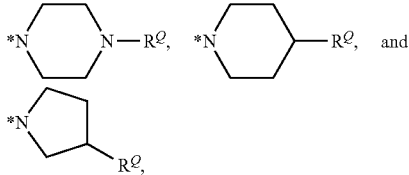

or a tautomer, an N-oxide, a hydrate, a solvate, or a salt thereof, or a mixture of any of the foregoing.

4. The compound according to claim 1, wherein:
$R^2$ is selected from:

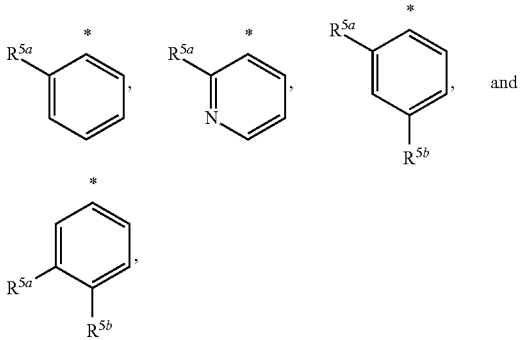

or a tautomer, an N-oxide, a hydrate, a solvate, or a salt thereof, or a mixture of any of the foregoing.

5. The compound according to claim 1, wherein:
$R^{5a}$ is a group selected from: methoxy-, ethoxy-, and $F_3C$—$CH_2$—O—,
or a tautomer, an N-oxide, a hydrate, a solvate, or a salt thereof, or a mixture of any of the foregoing.

6. The compound according to claim 1, wherein:
$R^{5b}$ is a group selected from: —C(=O)N(H)R$^8$, —C(=O)NR$^8$R$^7$, R$^8$—S(=O)—, R$^8$—S(=O)$_2$—, and —S(=O)(=NR$^7$)R$^8$,
or a tautomer, an N-oxide, a hydrate, a solvate, or a salt thereof, or a mixture of any of the foregoing.

7. The compound according to claim 1, wherein:
$R^6$ represents is a group selected from: —(CH$_2$)$_q$-phenyl, and —(CH$_2$)$_q$—(C$_3$-$C_6$-cycloalkyl), wherein said group is optionally substituted with a halogen atom,
or a tautomer, an N-oxide, a hydrate, a solvate, or a salt thereof, or a mixture of any of the foregoing.

8. The compound according to claim 1, wherein:
$R^7$ is a $C_1$-$C_3$-alkyl-group;
$R^8$ is a $C_1$-$C_6$-alkyl- or $C_3$-$C_6$-cycloalkyl-group,
or a tautomer, an N-oxide, a hydrate, a solvate, or a salt thereof, or a mixture of any of the foregoing.

9. The compound according to claim 1, wherein:
$R^7$ and $R^8$ are taken together with the molecular fragment to which they are attached to form a 4- to 6-membered heterocycloalkyl-group, which is optionally substituted with a $C_1$-$C_3$-alkyl-group,
or a tautomer, an N-oxide, a hydrate, a solvate, or a salt thereof, or a mixture of any of the foregoing.

10. The compound according to claim 1, wherein:
q is 1,
or a tautomer, an N-oxide, a hydrate, a solvate, or a salt thereof, or a mixture of any of the foregoing.

11. The compound according to claim 1, which is selected from the group consisting of:
4-(2-{[2-ethoxy-4-(ethylcarbamoyl)phenyl]amino}[1,2,4]triazolo[1,5-a]pyridin-6-yl)-N-(4-fluorobenzyl)piperazine-1-carboxamide;
4-(2-{[4-(tert-butylcarbamoyl)-2-(2,2,2-trifluoroethoxy)phenyl]amino}[1,2,4]-triazolo[1,5-a]pyridin-6-yl)-N-(4-fluorobenzyl)piperazine-1-carboxamide;
4-(2-{[4-(diethylcarbamoyl)-2-methoxyphenyl]amino}[1,2,4]triazolo[1,5-a]pyridin-6-yl)-N-(4-fluorobenzyl)piperazine-1-carboxamide;
4-(2-{[2-ethoxy-4-(morpholin-4-ylcarbonyl)phenyl]amino}[1,2,4]triazolo[1,5-a]pyridin-6-yl)-N-(4-fluorobenzyl)piperazine-1-carboxamide;
4-(2-{[4-(diethylcarbamoyl)-2-propoxyphenyl]amino}[1,2,4]triazolo[1,5-a]pyridin-6-yl)-N-(4-fluorobenzyl)piperazine-1-carboxamide;
4-(2-{[4-(diethylcarbamoyl)-2-(2-methylpropoxy)phenyl]amino}[1,2,4]triazolo [1,5-a]pyridin-6-yl)-N-(4-fluorobenzyl)piperazine-1-carboxamide trifluoroacetate;
4-(2-{[2-(cyclopropylmethoxy)-4-(diethylcarbamoyl)phenyl]amino}[1,2,4]triazolo [1,5-a]pyridin-6-yl)-N-(4-fluorobenzyl)piperazine-1-carboxamide;
4-(2-{[4-(diethylcarbamoyl)-2-(2-methoxyethoxy)phenyl]amino}[1,2,4]triazolo[1,5-a]pyridin-6-yl)-N-(4-fluorobenzyl)piperazine-1-carboxamide;
4-(2-{[4-(diethylcarbamoyl)-2-(2,2,2-trifluoroethoxy)phenyl]amino}[1,2,4]triazolo [1,5-a]pyridin-6-yl)-N-(4-fluorobenzyl)piperazine-1-carboxamide trifluoroacetate;

N-(4-fluorobenzyl)-4-(2-{[2-methoxy-4-(4-methylpiperazin-1-yl)phenyl]amino}-[1,2,4]triazolo[1,5-a]pyridin-6-yl)piperazine-1-carboxamide;

N-(4-fluorobenzyl)-4-(2-{[3-methoxy-4-(morpholin-4-ylcarbonyl)phenyl]-amino}[1,2,4]triazolo[1,5-a]pyridin-6-yl)piperazine-1-carboxamide;

N-(4-fluorobenzyl)-4-{2-[(2-methoxypyridin-3-yl)amino][1,2,4]triazolo[1,5-a]pyridin-6-yl}piperazine-1-carboxamide;

4-{2-[(2-ethoxypyridin-3-yl)amino][1,2,4]triazolo[1,5-a]pyridin-6-yl}-N-(4-fluoro-benzyl)piperazine-1-carboxamide;

4-{2-[(2-cyanophenyl)amino][1,2,4]triazolo[1,5-a]pyridin-6-yl}-N-(4-fluoro-benzyl)piperazine-1-carboxamide;

1-(2-{[2-ethoxy-4-(morpholin-4-ylcarbonyl)phenyl]amino}[1,2,4]triazolo[1,5-a]pyridin-6-yl)-N-(4-fluorobenzyl)piperidine-4-carboxamide;

N-(cyclopropylmethyl)-1-(2-{[2-ethoxy-4-(ethylcarbamoyl)phenyl]amino}-[1,2,4]triazolo[1,5-a]pyridin-6-yl)piperidine-4-carboxamide;

N-(cyclopropylmethyl)-1-(2-{[2-ethoxy-4-(morpholin-4-ylcarbonyl)phenyl]-amino}[1,2,4]triazolo[1,5-a]pyridin-6-yl)piperidine-4-carboxamide;

N-(cyclopropylmethyl)-1-(2-{[2-(2,2,2-trifluoroethoxy)pyridin-3-yl]amino}-[1,2,4]triazolo[1,5-a]pyridin-6-yl)piperidine-4-carboxamide;

3-ethoxy-N-ethyl-4-{[6-(4-{[(4-fluorophenyl)acetyl]amino}piperidin-1-yl)-[1,2,4]triazolo [1,5-a]pyridin-2-yl]amino}benzamide;

N-[1-(2-{[2-ethoxy-4-(morpholin-4-ylcarbonyl)phenyl]amino}[1,2,4]triazolo [1,5-a]pyridin-6-yl)piperidin-4-yl]-2-(4-fluorophenyl)acetamide;

N-(1-{2-[(2-ethoxypyridin-3-yl)amino][1,2,4]triazolo[1,5-a]pyridin-6-yl}piperidin-4-yl)-2-(4-fluorophenyl)acetamide; and 1-(4-fluorobenzyl)-3-[1-(2-{[4-(morpholin-4-ylcarbonyl)-2-(2,2,2-trifluoroethoxy)phenyl]amino}[1,2,4]triazolo[1,5-a]pyridin-6-yl)pyrrolidin-3-yl]urea, or a tautomer, an N-oxide, a hydrate, a solvate, or a salt thereof, or a mixture of any of the foregoing.

12. A pharmaceutical composition comprising the compound according to claim 1, or a tautomer, an N-oxide, a hydrate, a solvate, or a pharmaceutically acceptable salt thereof, or a mixture of any of the foregoing, and a pharmaceutically acceptable diluent or carrier.

13. A pharmaceutical combination comprising:

the compound according to claim 1, or a tautomer, an N-oxide, a hydrate, a solvate, or a pharmaceutically acceptable salt thereof, or a mixture of any of the foregoing; and an agent selected from: a taxane, Docetaxel, Paclitaxel, or Taxol; an epothilone, Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, Flutamide, Cyproterone acetate, or Bicalutamide; Bortezomib; a platinum derivative, Cisplatin, or Carboplatin; Chlorambucil; Methotrexate; and Rituximab.

14. A method for treatment of a disease of uncontrolled cell growth, proliferation or survival, an inappropriate cellular immune response, or an inappropriate cellular inflammatory response, comprising administering to a patient in need thereof a therapeutically effective amount of the compound according to claim 1, or a tautomer, an N-oxide, a hydrate, a solvate, or a pharmaceutically acceptable salt thereof, or a mixture of any of the foregoing, wherein the uncontrolled cell growth, proliferation or survival, inappropriate cellular immune response, or inappropriate cellular inflammatory response is mediated by Mps-1.

15. The method according to claim 14, wherein the disease of uncontrolled cell growth, proliferation or survival, inappropriate cellular immune response, or inappropriate cellular inflammatory response mediated by Mps-1 is a haemotological tumour, a solid tumour or metastases thereof.

16. The method according to claim 15, wherein the haemotological tumour, solid tumour or metastases thereof is selected from leukemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and metastases thereof.

* * * * *